(12) United States Patent
Inouye et al.

(10) Patent No.: US 6,333,191 B1
(45) Date of Patent: Dec. 25, 2001

(54) NUCLEIC ACIDS SEQUENCE, STRESS-INDUCED PROTEINS AND USES THEREOF

(75) Inventors: Masayori Inouye, Bridgewater; Pamela Jones, Edison; Jean-Pierre Etchegaray, Society Hill; Weining Jiang, Edison, all of NJ (US); N. Stephen Pollitt, Los Altos, CA (US); Joel Goldstein, North Brunswick, NJ (US)

(73) Assignee: University of Medicine and Dentistry of New Jersey, Newark, NJ (US)

( * ) Notice: Subject to any disclaimer, the term of this patent is extended or adjusted under 35 U.S.C. 154(b) by 0 days.

(21) Appl. No.: 09/017,754

(22) Filed: Feb. 3, 1998

Related U.S. Application Data

(62) Division of application No. 08/203,806, filed on Mar. 1, 1994, now Pat. No. 5,714,525, which is a continuation-in-part of application No. 07/852,013, filed on Mar. 9, 1992, now abandoned, which is a continuation of application No. 07/310,332, filed on Feb. 13, 1989, now abandoned.

(51) Int. Cl.[7] ............................. C12N 15/00; C07H 17/00
(52) U.S. Cl. ........................................ 435/320.1; 536/23.1
(58) Field of Search ................................. 536/24.1, 23.1; 435/320.1

(56) References Cited

PUBLICATIONS

Goldstein et al. P.N.A.S. 87:283–287, Jan. 1990.*
Yee et al. Molecular Microbiology 11(5) 833–839, Mar. 1994.*
Maniak et al. Jan., 1988; Mol. Cell. Biol. 8(1):153–159.*
Remaut et al. 1981; Gene 15:81–93.*

* cited by examiner

*Primary Examiner*—Karen Cochrane Carlson
(74) *Attorney, Agent, or Firm*—Schnader Harrison Segal & Lewis LLP

(57) ABSTRACT

A family of stimuli-induced in particular stress or cold-shock induced genes and proteins are disclosed which have conserved amino acid domains. Nucleic acid sequences of the genes and the promoters are also described. Various utilities of the promoters and of the proteins are disclosed.

11 Claims, 18 Drawing Sheets

```
           *         *         *         *         *         *
  AGCTTTAATATAGCTCATGAAAGGTAAACATTGGCAGCTGAAGGGCCACGCAGACCATTT 60

*         *         *         *         *         *
  ATCCGGCAAAATTCCACGCGTAATCCGGTGGTAATTTCTTCTGCATCGCGGAGATTGAGC 120

*         *         *         *         *         *
  GCTGAAACATGAAGCTGGACATCGATACGACCATCGGATGGGGTGATAAGACCCTTGCCG 180

*         *         *         *         *         *
  CTTTTGCCGTCAAAGGTTTTGACAATTCCTGTCATTTTACGGGACAAAAAAATTCCTTAA 240

*         *         * -35     *         * -10     *
  TACTGATAACTTGGCGCACTATACACACGTTCCTGAAGAAAGCTATAGTTTTTTGATGGG 300
3 TRANSCRIPTION START SITES
           *         *         * -35     *         * -10     *
  GTTGAAGATGGCTGGATGTCTAAAATAAACATTGCTTCATATGTTCAACTATGCGTTAAT 360
                                                        COLD-SHOCK INDUCIBLE
           *         *         *         *         *         *
  GATTGCGTCGGTTTGAAGAACAGACGATATACGAAGTAGTTTACTAAACGAGTTCTCATT 420

*         *         *         *         *         *
  TCAGGTGTTATTCACTTATTCCTTCTTTGAGTCTCTCCAATAAAGTACGAAGTCGTTTCT 480

*         *         *         *         *
  GTTATGCAAACCATTTATGCCGAAAGGCTCAAGTTAAGGAATGTAGA ATGTCAAATAAA 539
                                                   MetSerAsnLys

*         *         *         *         *         *
  ATGACTGGTTTAGTAAAATGGTTTAACGCTGATAAAGTTTTCGGCTTTATTTCTCCTGTT 599
  MetThrGlyLeuValLysTrpPheAsnAlaAspLysGlyPheGlyPheIleSerProVal

*         *         *         *         *         *
  GATGGTAGTAAAGATGTGTTTGTGCATTTTTCTGCGATTCAGAATGATAATTATCGAACC 659
  AspGlySerLysAspValPheValHisPheSerAlaIleGlnAsnAspAsnTyrArgThr

*         *         *         *         *         *
  TTATTTGAAGGTCAAAAGGTTACCTTCTCTATAGAGAGTGGTGCTAAAGGTCCTGCAGCA 719
  LeuPheGluGlyGlnLysValThrPheSerIleGluSerGlyAlaLysGlyProAlaAla

*         *         *         *         *         *
  GCAAATGTCATCATTACTGATTAA AATTCATCGCTCGTCTGTATACGATAACGAAGAAG 778
  AlaAsnValIleIleThrAsp -

*         *         *         *         *         *
  GCTGATGCCTGAGTAGAGATACGGACAGAGTAGTGAATATTGGATCTCTTTAATAAAAAG 838

*         *         *         *
  TAAGGAGGTCCAATACATGAAACAATGGCTAGCATATTT 877      FIG. 5
```

```
CGGGATATCAGCAAAAGATATTTACCCCATTAATTTATTAGGATGTTTACATCGGATTTG  60
TGATTAAGCGTGGTATTATTTATTACGCGAAACGTTTCTCTCTTGAGGTTTTTGCTCATT 120
CATCAATTTTTCTTATTTTAAATTTACAATCCTTTGGGGATTGACTTCTCTTTAGGGTAA 180
TTAATAGCCGTTAACTGACTGTTTTATGAGAAAAAGTGATATAACTTTTTATTCATTGCA 240
TAGCAAAAAATGTGATATTGCACGCACTATGTAATAACTTCTCCCACTGGCCTGGAACAA 300
CTGAACTTATTGAACTATGTTAGAAAATACGCCAGTTTAAGTATCTGCCTGAACTGGCAA 360
GGTTAAGCACAATGATATATCGGCGCGTATTCCGTTGCATAAGTGTGCAAAAAAAGTGGA 420
AGACGTATCGAGATTTGTGCGTCTGATCGAGACATGTTTAAAAATGGCTTGCCATAATTA 480
ACGTTGTATGTGATAACAGATTTCGGGTTAAACGAGGTACAGTTCTGTTTATGTGTGGCA 540
TTTTCAGTAAAGAAGTCCTGAGTAAACACGTTGACGTTGAATACCGCTTCTCTGCCGAGC 600
CTTATATTGGTGCCTCATGCAGTAATGTGTCAGTTTTATCTATGTTATGCCTGCGGCGAA 660
GAAAACAATCTAAGGAATTTTTCAA  ATGGCAAAGATTAAAGGTCAGGTTAAGTGGTTC 718
                           MetAlaLysIleLysGlyGlnValLysTrpPhe
AACGAGTCTAAAGGTTTTGGCTTCATTACTCCGGCTGATGGCAGCAAAGATGTGTTCGTA 778
AsnGluSerLysGlyPheGlyPheIleThrProAlaAspGlySerLysAspValPheVal
CACTTCTCCGCTATCCAGGGTAATGGCTTAAAAACTCTGGCTGAAGGTCAGAACGTTGAG 838
HisPheSerAlaIleGlnGlyAsnGlyPheLysThrLeuAlaGluGlyGlnAsnValGlu
TTCGAAATTCAGGACGGCCAGAAAGGTCCGGCAGCTGTTAACGTAACAGCTATCTGA TC 897
PheGluIleGlnAspGlyGlnLysGlyProAlaAlaValAsnValThrAlaIle  -
GAATCCACTGATCTGAAGTGTGAATACGCTTCAATCTCGCTATAAAGCCTCGTCGAATGC 957
GAGGCTTTTTACTATGCTTTATCTTCGCTCCTGGCGTTCGGATATTTGCCCGCCGCGTGA 1017
TTCGCGTTACACTTGCGGCCTTTAGTATCTGCCGGAGTTGTCATGTCTTTTTCCTGTCCA 1077
CTTTGCCATCAGCCTCTTTCGCGTGAAAAAAACAGCTATATCT 1120
```

FIG. 5A

```
            -35                        -10
cspA     TTGCAT  ← 17bp →  CTTAAT -35                        -10
cspB     TTGCTT  ← 17bp →  GTTAAT CONSENSUS TRANSCRIPTION START SIGNAL:
         TTGACA  ← 17bp →  TATAAT
```

FIG. 7

```
                              10        20        30
                              *         *         *
E. coli          CspA    MSGKMTGIVKWFNADKGFGFITPDDGSKDVFVHFSAI
E. coli          CspB    ••N••L•••••••••••••••••••S•V••••••••
E. coli          CspC    ••A IK•Q•••••ES•••••••••••A•••••••••
E. coli          CspD    ---EK•T•••NA•••••••••C•EG•GE I•A•Y•T•
S. clavuligerus  SC7.0   ---A •T • E ••••••C•EG•GE I•A•Y•T•
B. subtilis      CspB    ---LE•K••SE••••••••AQ•G•GP•••Y••
H. sapiens       YB1     IAT•VL•T••••VRN•Y•••NR••TKE••••Q•T•

40        50        60        70
                              *         *         *         *
CspA    QNDG---Y-KSLDEGQKVSFTIESGAKGPAAGNVTSL
CspB    ••NDG---N----•-RT•F•••T•S•••••••A••IITD
CspC    •GN-•---F-•T•A•••NE•E•QD•Q•••••V••AI
CspD    •M••-•---•-RT•KA••S•Q•DVHQ•P••NH•SVIVPVEVEAAVA
SC7.0   NAT•-•---F-R•E••N•V•N•DVTH•E-••Q•E••SPA
CspB    •GE•-•---F-•T•E••A••E•VE•NR••Q•A••KEA
YB1     KKNNPRK•LR•VGD•ET•E•DVVE•E•EE•A•••GP
```

FIG. 10

```
          *         *         *         *         *         *
AGCTTTAATATAGCTCATGAAAGGTAAACATTGGCAGCTGAAGGGCCACGCAGACCATTT 60

*         *         *         *         *         *
ATCCGGCAAAATTCCACGCGTAATCCGGTGGTAATTTCTTCTGCATCGCGGAGATTGAGC 120

*         *         *         *         *         *
GCTGAAACATGAAGCTGGACATCGATACGACCATCGGATGGGGTGATAAGACCCTTGCCG 180

*         *         *         *         *         *
CTTTTGCCGTCAAAGGTTTTGACAATTCCTGTCATTTTACGGGACAAAAAAATTCCTTAA 240

*         *         *         *         *         *
TACTGATAACTTGGCGCACTATACACACGTTCCTGAAGAAAGCTATAGTTTTTTGATGGG 300

*         *         *         *         *         *
GTTGAAGATGGCTGGATGTCTAAAATAAACATTGCTTCATATGTTCAACTATGCGTTAAT 360

*         *         *         *         *         *
GATTGCGTCGGTTTGAAGAACAGACGATATACGAAGTAGTTTACTAAAGCAGTTCTCATT 420

*         *         *         *         *         *
TCAGGTGTTATACACTTATTCCTTCTTTGAGTCTCTCCAATTAAGTACGAAGTCGTTTCT 480

*         *         *         *         *
GTTATGCAAACCATTTATGCCGAAAGGCTCAAGTTAAGGAATGTAGA ATGTCAAATAAA 539
                                                MetSerAsnLys

*         *         *         *         *         *
ATGACTGGTTTAGTAAAATGGTTTAACGCTGATAAAGGTTTCGGCTTTATTTCTCCTGTT 599
MetThrGlyLeuValLysTrpPheAsnAlaAspLysGlyPheGlyPheIleSerProVal

*         *         *         *         *         *
GATGGTAGTAAAGATGTGTTTGTGCATTTTPCTGCGATTCAGAATGATAATTATCGAACC 659
LeuPheGluGlyGlnLysValThrPheSerIleGluSerGlyAlaLysGlyProAlaAla

*         *         *         *         *         *
GCAATAGTCATCATTACTGATTAA AATTCATCGCTCGTCTGTATACGATAACGAAGAAG 778
AlaAsnValIleIleThrAsp -

*         *         *         *         *         *
GCTGATGCCTGAGTAGAGATACGGACAGAGTAGTGAATATTGGATCTCTTTAATAAAAAG 838

*         *         *         *
TAAGGAGGTCCAATACATGAAACAATGGCTAGCATATTT 877        FIG. 11
```

```
CGGGATATCAGCAAAAGATATTTACCCCATTAATTTATTAGGATGTTTACATCGGATTTG  60

TGATTAAGCGTGGTATTATTTATTACGCGAAACGTTTCTCTCTTGAGGTTTTTGCTCATT 120

CATCAATTTTTCTTATTTTAAATTTACAATCCTTTGGGGATTGACTTCTCTTTAGGGTAA 180

TTAATAGCCGTTAACTGACTGTTTTATGAGAAAAAGTGATATAACTTTTTATTCATTGCA 240

TAGCAAAAAATGTGATATTGCACGCACTATGTAATAACTTCTCCCACTGGCCTGGAACAA 300

CTGAACTAATTGAACTATGTTAGAAAATACGCCAGTTTAAGTATCTGCCTGAACTGGCAA 360

GGTTAAGCACAATGATATATCGGCGCGTATTCCGTTGCATAAGTGTGCAAAAAAAGTGGA 420

AGACGTATCGAGATTTGTGCGTCTGATCGAGACATGTTTAAAAATGGCTTGCCATAATTA 480

ACGTTGTATGTGATAACAGATTTCGGGTTAAACGAGGTACAGTTCTGTTTATGTGTGGCA 540

TTTTCAGTAAAGAAGTCCTGAGTAAACACGTTGACGTTGAATACCGCTTCTCTGCCGAGC 600

CTTATATTGGTGCCTCATGCAGTAATGTGTCAGTGTTATCTATGTTATGCCTGCGGCGAA 660

GAAAACAATCTAAGGAATTTTTCAA   ATGGCAAAGATTAAAGGTCAGGTTAAGTGGTTC 718
                            MetAlaLysIleLysGlyGlnValLysTrpPhe

AACGAGTCTAAAGGTTTTGGCTTCATTACTCCGGCTGATGGCAGCAAAGATGTGTTCGTA 778
AsnGluSerLysGlyPheGlyPheIleThrProAlaAspGlySerLysAspValPheVal

CACTTCTCCGCTATCCAGGGTAATGGCTTCAAAACTCTGGCTGAAGGTCAGAACGTTGAG 838
HisPheSerAlaIleGlnGlyAsnGlyPheLysThrLeuAlaGluGlyGlnAsnValGlu

TTCGAAATTCAGGACGGCCAGAAAGGTCCGGCAGCTGTTAACGTAACAGCTATCTGA TC 897
PheGluIleGlnAspGlyGlnLysGlyProAlaAlaValAsnValThrAlaIle -

GAATCCACTGATCTGAAGTGTGAATACGCTTCAATCTCGCTATAAAGCCTCGTCGAATGC 957

GAGGCTTTTTACTATGCTTTATCTTCGCTCCTGGCGTTCGGATATTTGCCCGCCGCGTGA 1017

TTCGCGTTACACTTGCGGCCTTTAGTATCTGCCGGAGTTGTCATGTCTTTTTCCTGTCCA 1077

CTTTGCCATCAGCCTCTTTCGCGTGAAAAAAACAGCTATATCT 1120
```

FIG. 12

```
            *         *         *         *         *         *
AAGCTTCGATGCAATTCACGATCCCGCAGTGTGATTTGAGGAGTTTTCAATGGAATATAA      60
            *         *         *         *         *         *
AGATCCAATGCATGAGCTGTTGAGCAGCCTGGAACAGATTGTTTTTAAAGATGAAACGCA     120
            *         *         *         *         *         *
GAAAATTACCCTGACGCACAGAACAACGTCCTGTACCGAAATTGAGCAGTTACGAAAAGG     180
            *         *         *         *         *         *
GACAGGATTAAAAATCGATGATTTCGCCCGGGTTTTGGGCGTATCAGTCGCCATGGTAAA     240
            *         *         *         *         *         *
GGAATGGGAATCCAGACGCGTGAAGCCTTCAAGTGCCGAACTAAAATTGATGCGTTTGAT     300
            *         *         *         *         *         *
TCAAGCCAACCCGGCATTAAGTAAGCAGTTGATGGAATAGACTTTATCCACTTATGCTGT     360
            *         *         *         *         *         *
TTACGGTCCTGATGACAGACCGTTTTCCAACCGATTAATCATAAATATGAAAAATAATTG     420
            *         *         *         *         *         *
TTGCATCACCCGCCAATGCGTGGCTTAATGCACATCAACGGTTTGACGTACAGACCATTA     480
            *         *         *         *         *         *
AAGCAGTGTAGTAAGGCAAGTCCCTTCAAGAGTTATCGTTGATACCCCTCGTAGTGCACA     540
            *         *         *         *         *         *
TTCCTTTAACGCTTCAAAATCTGTAAAGCACGCCATATCGCCGAAAGGCACACTTAATTA     600
            *         *         *         *         *
TTAAAGGTAATACACT   ATGTCCGGTAAAATGACTGGTATCGTAAAATGGTTCAACGCT     658
                  MetSerGlyLysMetThrGlyIleValLysTrpPheAsnAla
       *         *         *         *         *         *
GACAAAGGCTTCGGCTTGATCACTCCTGACGATGGCTCTAAAGATGTGTTCGTACACTTC     718
AspLysGlyPheGlyPheIleThrProAspAspGlySerLysAspValPheValHisPhe
       *         *         *         *         *         *
TCTGCTATCCAGAACGATGGTTACAAATCTCTGGACGAAGGTCAGAAAGTGTCCTTCACC     778
SerAlaIleGlnAsnAspGlyTyrLysSerLeuAspGluGlyGlnLysValSerPheThr
       *         *         *         *         *         *
ATCGAAAGCGGCGCTAAAGGCCCGGCAGCTGGTAACGTAACCAGCCTGTAA   TCTCTGC     836
IleGluSerGlyAlaLysGlyProAlaAlaGlyAsnValThrSerLeu -
       *         *         *         *         *         *
TTAAAAGCACAGAATCTAAGATCCCTGCCATTTGGCGGGGATTTTTTATTTGTTTTCAG     896
       *         *         *         *         *         *
GAAATAAATAATCGATCGCGTAATAAAATCTATTATTATTTTTGTGAAGAATAAATTTGG     956
       *         *         *         *         *         *
GTGCAATGAGAATGCGCAACGCCGTAAGTAAGGCGGGAATAATTTCCCGCCGAAGACTCT    1016
       *         *         *         *         *         *
TACTCTTTCAATTTGCAGGCTAAAAACGCCGCCAGCTCATAACTCTCCTGTTTAATATGC    1076
       *         *         *         *         *         *
AATTCACACAGTGAATCTCTTATCATCCAGGTGAAAAATAAAAGCGTGAAACAAATCACT    1136
       *         *         *         *         *         *
ATTAAAGAAAGTAATCTATATTTCTGCGCATTCCAGCTCTGTGTTGATTTCACGAGTATG    1196
       *
TACTGCACC    1205
```

FIG. 16

NUCLEIC ACIDS SEQUENCE, STRESS-INDUCED PROTEINS AND USES THEREOF

This is a divisional application of allowed patent application Ser. No. 08/203,806 filed Mar. 1, 1994 which is incorporated herein by reference in its entirety, now U.S. Pat. No. 5,714,575, issued Feb. 3, 1998, which is a continuation-in-part application of Ser. No. 07/852,013, filed Mar. 9, 1992, abandoned, which is a continuation application of application Ser. No. 07/310,332, filed Feb. 13, 1989, abandoned, all applications being incorporated by reference.

Publications and manuscripts which are attached and co-filed herewith are also incorporated by reference in their entirety.

The parent application discloses cold-shock proteins which are induced by cold-shock following a shift to lower temperature from physiological growth temperatures. *E. coli* was shown to grow at low temperatures after cold-shock induction. Other features of these proteins and their promoters are disclosed in the parent application.

SUMMARY OF THE INVENTION

The present invention further describes these and other members of a family of stress-induced, in particular cold-shock induced proteins (Csp), their synthesis following a shift from physiological growth temperature of a microorganism to temperatures below physiological, nucleotide sequences of stress-induced and cold-shock genes, deduced amino acid sequences thereof and cold-shock induced and other promoters. The invention also describes the expression of proteins other than the cold-shock proteins under the direction of cold-shock promoters. Various utilities of the cold-shock proteins and promoters are described.

BRIEF DESCRIPTION OF THE FIGURES

FIG. 5 shows the nucleotide sequence of CspB and the deduced amino acid sequence of CspB protein.

FIG. 5A shows the nucleotide sequence of CspC and its deduced amino acid sequence.

FIG. 7 shows the CspA leader region.

FIG. 10 shows a comparison of *E. coli* CspA with other CspA-like proteins.

FIG. 11 shows the nucleotide sequence and the deduced amino acid sequence of CspB.

FIG. 12 shows the nucleotide sequence and the deduced amino acid sequence of CspC.

FIG. 16 shows the partial nucleotide sequence of the cloned HindIII fragment, including the region encoding CspA and the corresponding amino acid sequence. The sequence shown corresponds to SEQ. ID 19 and SEQ. ID 20 in the sequence listing.

DESCRIPTION OF THE PREFERRED EMBODIMENTS

Figure 1:
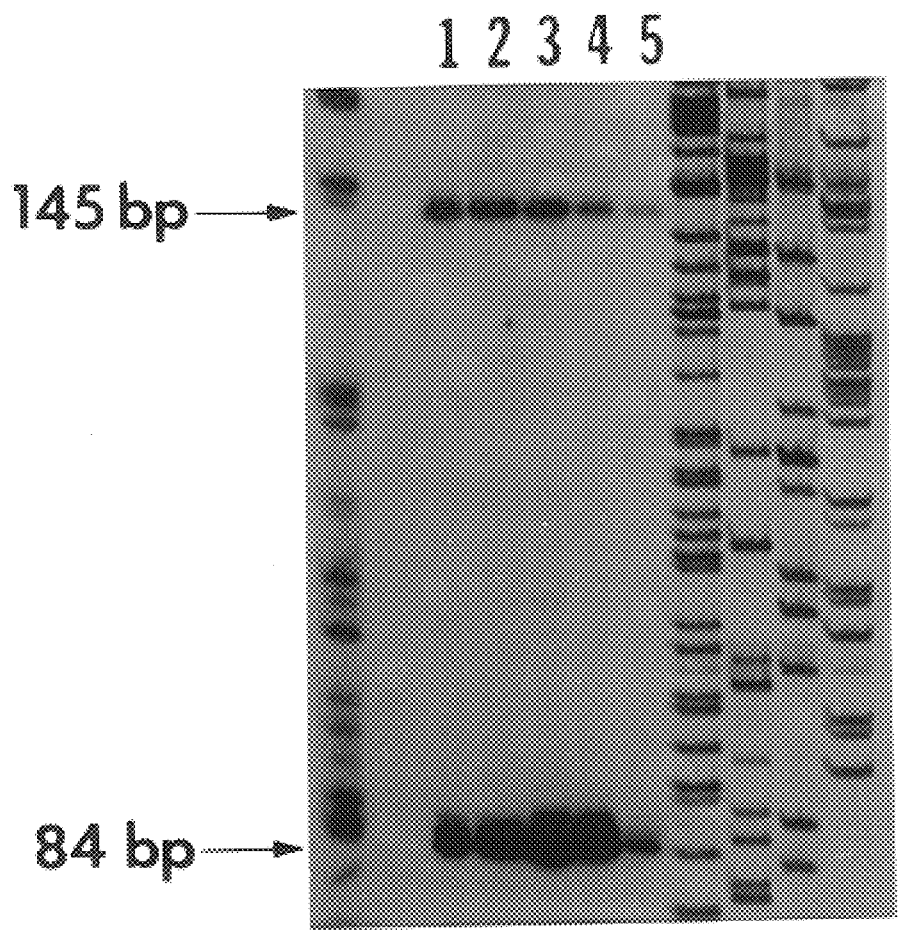
FIG. 1 shows a primer extension assay with an 84 nucleotide transcript and a 145 nucleotide transcript.

A manuscript entitled "The Cold-shock Response—"A Hot Topic" Jones and Inouye, *Molecular Microbiology*, 1994 (in press) (hereinafter "Hot Topic") co-filed herewith is incorporated herein by reference in its entirety and a second manuscript entitled "Family of the Major Cold-Shock Protein, CspA (CS7.4) of *Escherichia coli* Which Shows a High Sequence Similarity with the Eukaryotic Y-Box Binding Proteins", Lee et al. (in press) (hereinafter "Family") and the galley proof thereof are also co-filed herewith and incorporated by reference in their entirety. An untitled report including 7 Figures (hereinafter "Report") is also co-filed herewith and incorporated by reference in its entirety.

Publications of interest are listed under "References" are incorporated herein by reference. Those co-filed herewith are marked with an asterisk.

Studies carried out in conjunction with the invention have focused on the physiology of *E. coli* at low temperature with the initial discovery of the cold-shock response following the shift from 37° C. to 10° C. The cold-shock response describes a specific pattern of gene expression in response to downshift in temperature from the physiological growth temperature of the organism. This pattern includes the induction of a family of proteins called "cold-shock proteins" (Csp), continued synthesis of transcriptional and translational proteins despite the lag period, and specific repression of heat shock proteins.

The synthesis of individual proteins following a shift from 37 to 10° C. is shown on the autoradiograms of FIG. 9. Proteins whose-differential rate of synthesis increased, i.e. the cold-shock proteins, are enclosed in boxes. Other proteins that were continuously synthesized, which include many transcriptional and translational proteins, are designated by arrows. Heat shock proteins DnaK and GroEL, whose synthesis was repressed are enclosed in circles. Jones et al. 1987, Jones et al. 1992a.

After the shift to 10° C., the response reaching maximum induction during the 3rd hour post shift followed by resumption of protein synthesis and growth after the 4th hour. The cold-shock response is induced with any 13° C. downshift or more. Generally, the magnitude of the induction is dependent upon the range of the temperature shift; the larger the range of the temperature shift, the more pronounced the response. Like the heat shock response, it is believed that the cold-shock response also serves an adaptive function.

The cold-shock response affects heat-shock proteins. It has been observed that a drop in temperature from physiological growth temperature to 13° C. is also characterized by a specific repression of heat-shock proteins (Jones et al. 1992). Repression of heat shock proteins has also been observed under conditions that cause both a decrease in the translational capacity of the cell and stimulation of ribosome formation, such as depriving streptomycin from a streptomycin-dependent mutant, or adding tetracycline to a partially tetracycline-resistant strain, or following a nutritional shift-up (Schnier, 1987). Other similar conditions that cause a decrease in the translational capacity and an increase in ribosomal protein synthesis, such as the addition of chloramphenicol or tetracycline to sensitive strains of E. coli, resulted in the induction of cold-shock proteins as well as repression of heat shock proteins in eukaryotes (VanBogelen & Neidhardt, 1990).

Stress-induced i.e. cold and heat shock induced proteins have also been identified whose expression is increased after a shift from physiological growth temperature to about 10° C. These proteins, namely protein TIP1 have been described (Kondo and Inouye, 1991; Kowalski et al., 1993). Another identified cold-shock gene encodes a nucleolin-like protein called NSR1 (Kondo and Inouye, 1992). Since these and other proteinsz can be induced by various stimuli, they often are referred to as "stimuli"-induced.

Studies carried out in conjunction with the invention suggest that the state of the ribosome is the physiological center for the induction of the cold-shock response (VanBogelen and Neidhardt, 1990). Consistent with the proposed involvement of the (p)ppGPP level in the cold-shock response is the finding that many of the inhibitors of translation that induce the cold-shock response also result in a decrease in the (p)ppGpp level (Lund and Kjeldgaard, 1972). The prevailing model is that an abrupt downshift in temperature causes a physiological state where the translational capacity of the cell is insufficient relative to the supply of charged tRNA signalling a decrease in the (p)ppGpp level and the induction of the cold-shock response (Jones et al., 1992a). The observation that an inhibitor of initiation of translation is an inducer of the cold-shock response (Jones et al., 1992a) combined with the finding that low temperature inhibits initiation of translation (Friedman et al., 1971, Broeze et al., 1978) suggest that a partial block in initiation of translation may be responsible for the decreased translational capacity following a downshift in temperature (Jones et al., 1992a). The function of the cold-shock response is not known. A plausible function may be to overcome the partial block in translation, thereby increasing the translational capacity of the cell or vice versa.

A Family of Stress-Induced Proteins

A family of stress-induced proteins has been identified which is characterized by highly conserved common domains of amino acid sequences. FIG. 10 shows the comparison of the amino acid sequences of three proteins: CspA, CspB, CspC and CspD deduced from the DNA sequences of their genes. A first domain includes the sequence VKFWNFN. A second domain includes sequence K/NGF/YGFI. A third smaller domain includes sequence DV/IFV/AH and a forth domain which includes sequence E/DG/N/QE.

Figure 6:
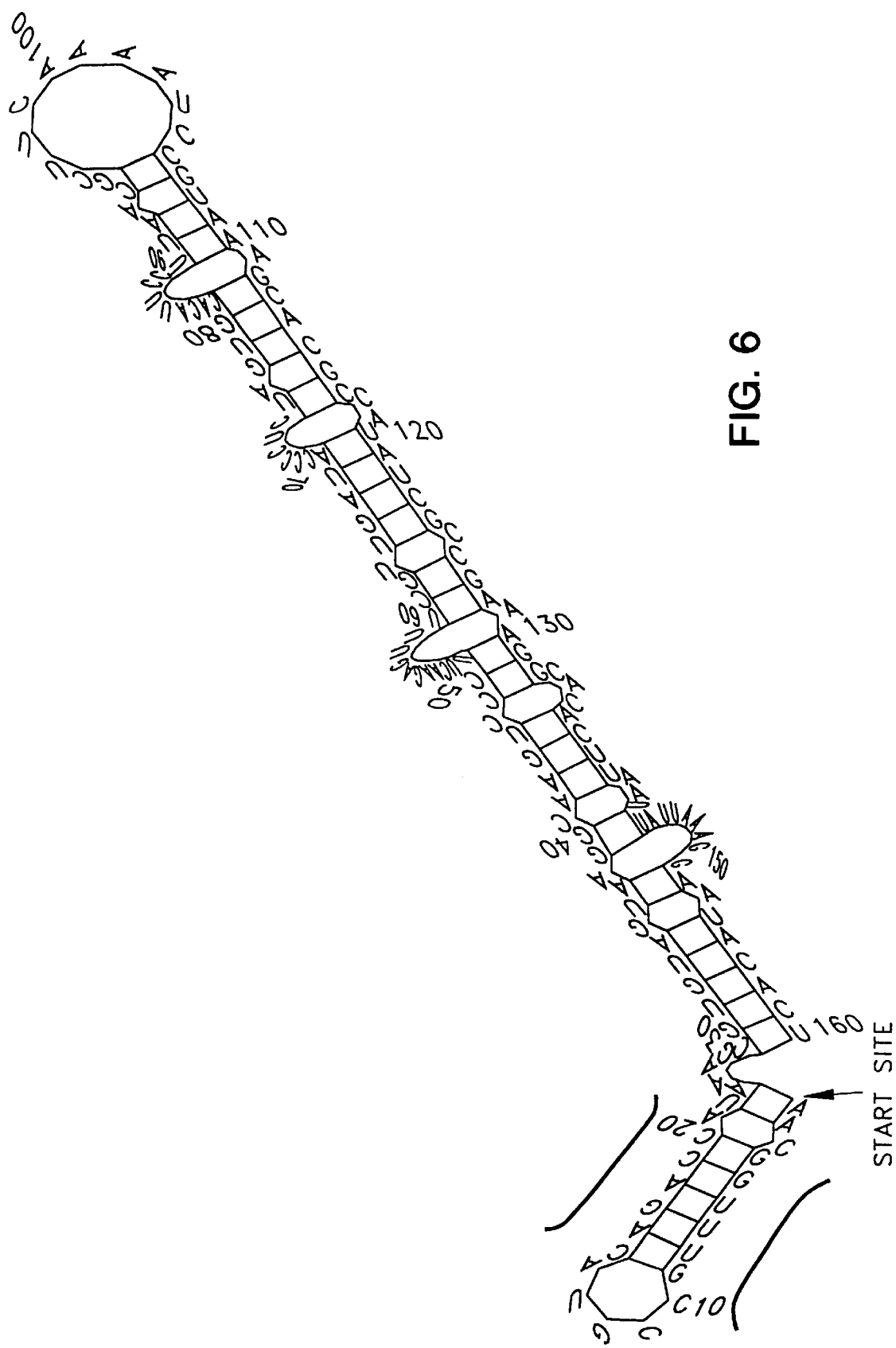
FIG. 6 shows the sequence of the −35 and −10 promoter regions of CspA and CspB compared with a consensus sequence of the transcription start signal of a prokaryote. Note the −35 similar domain.

FIG. 6 in the parent applicaton Ser. No. 07/852,013 and FIGS. 11 and 12 herein show the DNA sequence of CspA, CspB, CspC and the respective amino acid sequences deduced from the DNA sequences, respectively.

All proteins have a very high content of aromatic amino acids: two (WF) in the first domain; two (FF) in the second domain; and one (F) in the third domain. Further, it will be observed from FIG. 10 that the content of aromatic acids of the proteins shown is: 8 residues (6 Phe, 1 Tyr and 1 Trp) for CspA; 9 residues (7 Phe, 1 Tyr and 1 Trp) for CspB; 8 residues (7 Phe, 0 Tyr, and 1 Trp) for CspC; and 8 residues (5 Phe, 2 Tyr and 1 Trp) for CspD. All 8 aromatic residues in CspA are conserved in all Csp proteins except for Phe-34 and Try-42 which are substituted with Tyr in CspD and Phe in CspC, respectively.

All Csp proteins contain only one conserved histidine residue (His-33 in CspA; except for CspD which contains 3). CspA, CspB, and CspC contain no cysteine residue, while CspD contains only one. All Csp proteins contain large numbers of charged residues: 16 (7 Lys, 0 Arg, 1 His, 2 Glu and 6 Asp) for CspA; 15 (6 Lys, 1 Arg, 1 His, 2 Glu and 5 Asp) for CspB; 15 (7 Lys, 0 Arg, 1 His, 4 Glu and 3 Asp) for CspC; and 17 (5 Lys, 1 Arg, 3 His, 5 Glu and 3 Asp) for CspD.

It is noteworthy that the sequence identities are higher in the amino terminal half than in the carboxyl-terminal half of the amino acid sequence. In the amino terminal half, there are found two highly and large conserved sequences, K/NGF/YGFI and DV/IFV/AH.

CspA, CpsB, CspC and CspD encode a polypeptide of 70, 71, 69 and 74 amino acid residues, respectively. CspB has 56 identical residues to CspA (79% identity); CspC has 48 identical to CspA (70% identity), and CspD has 33 identical residues to CspA (45% identity). The percentage identity can also be computed by omitting the carboxyl-terminal extra residues of CspD as being outside the cold-shock domain as defined by CspA.

It is conceivable that amino acids of similar structures be interchangeable, for instance, Val by Ile or Leu; or Ser by Thr, and that aromatic amino acids be interchangeable with other aromatic amino acids, for instance, possibly Phe by Tyr, and aliphatic amino acids by other aliphatic amino acids. It is conceivable also that in the conserved domain(s), odd amino acid(s) can be replaced by one or more amino acids to make the domain fully or closer to fully homologous, for instance in the third domain Ile or Ala by Val or in the fifth domain, Ala or Asn by Glu or Gly.

By synthesis of these proteins or by appropriate substitution(s) in the nucleic acid sequences therefor, this can be readily performed so that any one of these proteins can be made the functionally equivalent or closer to another.

These unique features of these Csp proteins are likely to play important roles in the function and utility of these proteins. Individual Csp proteins can form dimers. Accordingly, it is believed that various heterodimers may be formed between different Cps proteins, which can be important for functional versatility of Csp proteins. Further, as discussed, CspA contains aromatic (and basic) residues. See in FIG. 10: K10, W11, K16, F18, F20, F31, H33, F34 and K60. It is possible that the aromatic residues that are found on the surfaces of the proteins play a role in the function of the Csps and, in particular in their interaction with their targets. The three dimensional structures of CspA determined by x-ray crystallography and NMR spectroscopy indicate that the protein comprises five antiparallel b-sheet structures, and that aromatic residues exposed on the surface of the protein interact with single-stranded DNA.

The Csps are believed to have the capacity to interact with ssDNA or RNA, possibly to unwind the secondary structures of these molecules and stabilize their primary structures. The Csp proteins have been reported to contain the RNA binding RNP1 sequence motif, [G-A]-[F-Y]-[G-A]-[F-Y]-[IVA]. Lansdman, 1992. Further, a putative ATP-dependent helicase is induced upon cold-shock, suggesting a specific requirement for "RNA chaperons" at low temperature. Further, it has been demonstrated that CspA recognizes a specific DNA sequence. Jones et al. 1992b. Csp proteins thus may be essential for the transcriptional machinery at low temperature in such a way to convert the closed DNA or RNA complex to an open complex during initiation of transcription. Another possible function of Csp proteins is their involvement in masking group of mRNAs to inhibit their translation.

Other uses for the members of the Csp family include the staining of DNA. The property of members of the Csp family to bind DNA and RNA indicate the potential use of these proteins in visualization of DNA in agarose and acrylamide gels. Standard procedures include the use of carcinogenic stains such as ethidium bromide. Members of the Csp family complexed with a fluorescent dye can potentially be used to safely stain DNA. The proteins can also be useful in the stabilization of DNA and RNA. The ability of the proteins to stabilize the primary structure of RNA and DNA indicate the potential use of these proteins in increasing the efficiency of DNA and RNA in various in vitro reactions. Also, these proteins can act as denaturases. Their property to unwind secondary structure in RNA or DNA indicate the potential use of these proteins to denature DNA irrespective of temperature.

The Csp proteins therefore can be seen to have very important potential commercial uses.

Promoters

Parent patent application Ser. No. 07/852,013 which is incorporated herein by reference describes the cold-induced promoter for CspA. The promoter of the invention is believed to be located on the cloned HindIII fragment between nucleotides 1 and 605. The first 997 bp of the cloned HindIII fragment contains all the necessary elements of the functional gene for regulated expression including the ribosome binding sites.

There is evidence of a promoter sequence at −35 and −10 upstream of the coding region, at positions 330 and 355, respectively. Another characteristic of the promoter is that it responds to a drop in temperature.

The promoter of the invention is activated at reduced temperature and directs transcription of the gene of the invention.

The promoter of the invention is activated at reduced temperature and directs transcription of the gene of the invention.

The promoter of the invention is cold-inducible in vivo and is recognized in vivo by RNA polymerase.

Parent patent application Ser. No. 07/852,013 which is incorporated herein by reference describes the cold-induced promoter For CspA. The −10 and −35 regions CTTATT and TTGCAT of the promoter sequence are shown in FIG. 6B of that application. The promoter was shown to control the expression of β-galactosidase. A plasmid (pKM005) carrying the lacZ gene without promoter was compared with the plasmid carrying CspA promoter on a 806 bp HindIII-PvuII fragment. The induction by temperature shift from 37° C. to 15° and to 10° C. showed a significant increase (65%) in β-galactoside expression from *E. coli* cells harboring the plasmid carrying the CspA promoter.

In the above-described embodiment of the invention, the CspA promoter of the invention has been used in a classic model to control the expression of β-galactosidase, For this purpose, a plasmid (pKM005) containing the lacZ structural gene without promoter was compared with the plasmid containing the CspA promoter on an 806 bp HindIII-PvuII fragment (pJJG04).

A second plasmid, pJJG08, was constructed which contains a smaller nucleotide fraction of the upstream region of the CspA gene, terminating at the ApaLI site (bp 534) (SEQ ID NO:14). The results are shown in Table I.

TABLE I

RESULTS OF EXPRESSION IN LAC STRAIN

| Plasmid | TEMPERATURE 37° | AFTER SHIFT to 15° | AFTER SHIFT to 10° |
|---|---|---|---|
| pKM005 | 6.7 | 4.1 | 3.7 |
| pJJG04 | 549.0 | 900.0 | 851.0 |
| pJJG08 | 40.7 | 45.6 | 56.1 |

Temperature are in ° C.: other numerals refer to "Units" of enzyme activity.

The results show that the cspA promoter is capable of directing a heterologous gene to express a selected protein.

Likewise, all other Csp genes were studies for their ability to express β-galactosidase. All Csp genes tested were fused in the coding regions with the lacZ gene and the expression of β-galactosidase was examined for these hybrid genes upon cold-shock. The plasmids were transformed into *E. coli*.

Cold-shock induction was observed for CspB as for CspA. Curiously, not for CspC and not for CspD. It is postulated that induction of these genes is stress-induced.

Figure 15:
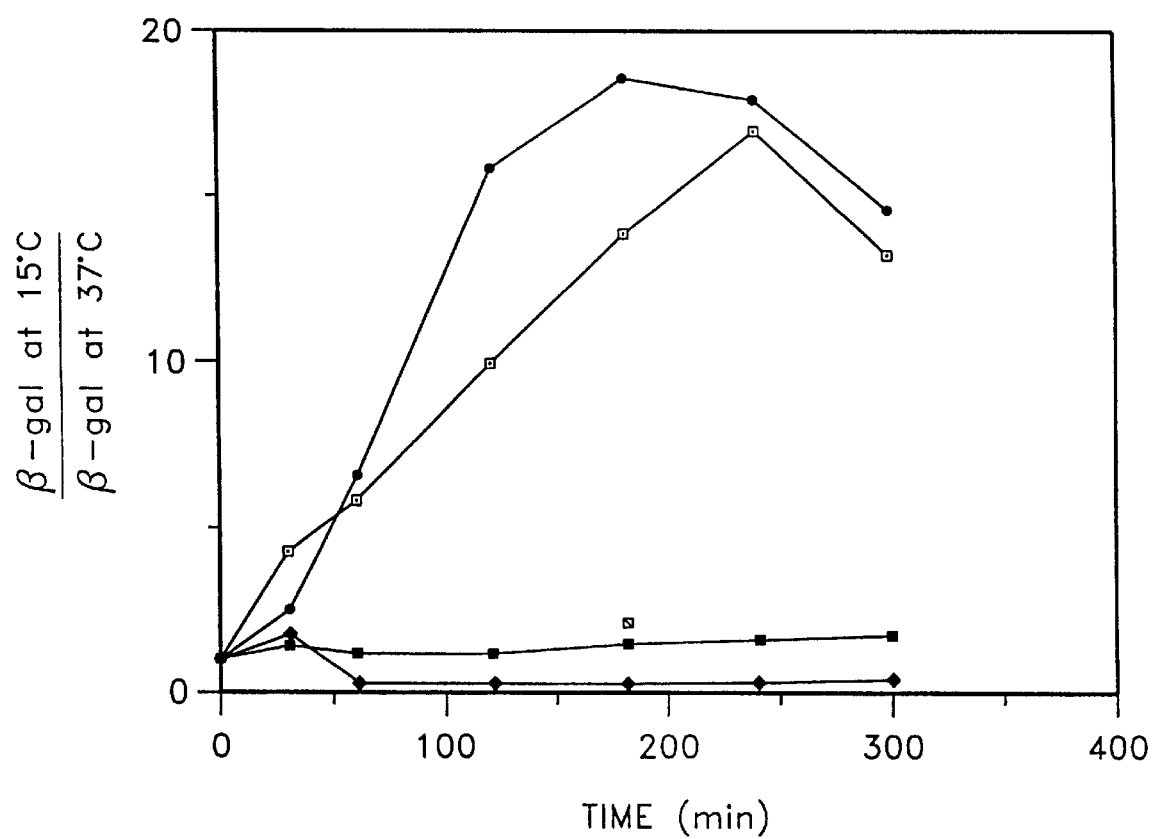
FIG. 15. shows β-galactosidase induction of Csp-lacZ translation fusions after temperature shift from 37° C. to 15° C. At a mid-exponential phase, cultures of *E. coli* SG480 harboring various plasmids grown at 37° C. in L broth were transferd to a incubator-shaker at 15° C. One-ml samples were taken at times indicated for the β-galactosidase assay (Miller, 1992).

FIG. 15 shows the respective β-galactosidase activities (assayed according to Miller (1972)) expressed as ratios of the β-galactosidase activity at 15° C. to that at 37° C. The activities at 0 time were 33, 65, 424 and 16 units for CspA, CspB, CspC and CspD, respectively. The activity of CspC is particularly noteworthy.

The construction of lacZ fusion with Csp genes proceeded as follows. To construct the fusion gene the following fragments were first amplified by polymerase chain reaction (PCR) for each Csp gene; from nucleotide 1 to 655 for CspA (Goldstein et al., 1990), from nucleotide 1 to 566 for CspB (FIG. 2), from nucleotide 1 to 721 for CspC (FIG. 2), and from nucleotide −696 to −330 for CspD (Gottesman et al., 1990). In the PCR reaction, both primers were designed to contain a BamHI site. In particular, the downstream BamHI sites for all Csp genes were designed to be created at the 11th codon of the Csp open-reading frames so that the first 10 amino acid sequences were fused in. phase to the lacZ coding region at codon 7 at the BamHI site of the pRS414 vector (Simons et al., 1987). The plasmids were transformed in *E. coli* SG480. β-galactosidase activity was assayed according to Miller (1972).

To investigate possible differences between CspA and CspB, and whether CspB is also transcriptionally regulated, time course primer extension experiments were performed. Cell cultures were grown at 37° C. to early logarithmic phase and then transferred to 15° C. Prior to shifting the culture to 15° C., an aliquot was removed and designated as time 0 sample of the time course. Samples were subsequently removed at 10, 45, 75 and 120 minutes, Total RNA was isolated from each culture and subjected to primer extension using a radiolabeled oligonucleotide that hybridizes to the 5' untranslated region of the CspB gene. Inspection of the primer extension assay revealed two products, an 84 nucleotide transcript and a 145 nucleotide transcript (FIG. 1A, lane 1). Interestingly, the levels of the 84 nucleotide mRNA dramatically increased during the cold-shock treatment, peaking at 45 to 75 minutes and finally declining by 120 minutes. In contrast, the 145 nucleotide product appeared to linearly decrease upon shift to 15° C. Thus, this analysis suggests that the CspB gene contains two transcription start sites; one which appears stimulated by cold-shock treatment and a second which is repressed under the same conditions. See FIG. 5 which shows the cold-shock inducible promoter region, the cold-shock repressed promoter region and three transcription start sites. Functionally equivalent promoters are stress—in particular cold-induced are considered within the scope of the invention.

Figure 2:
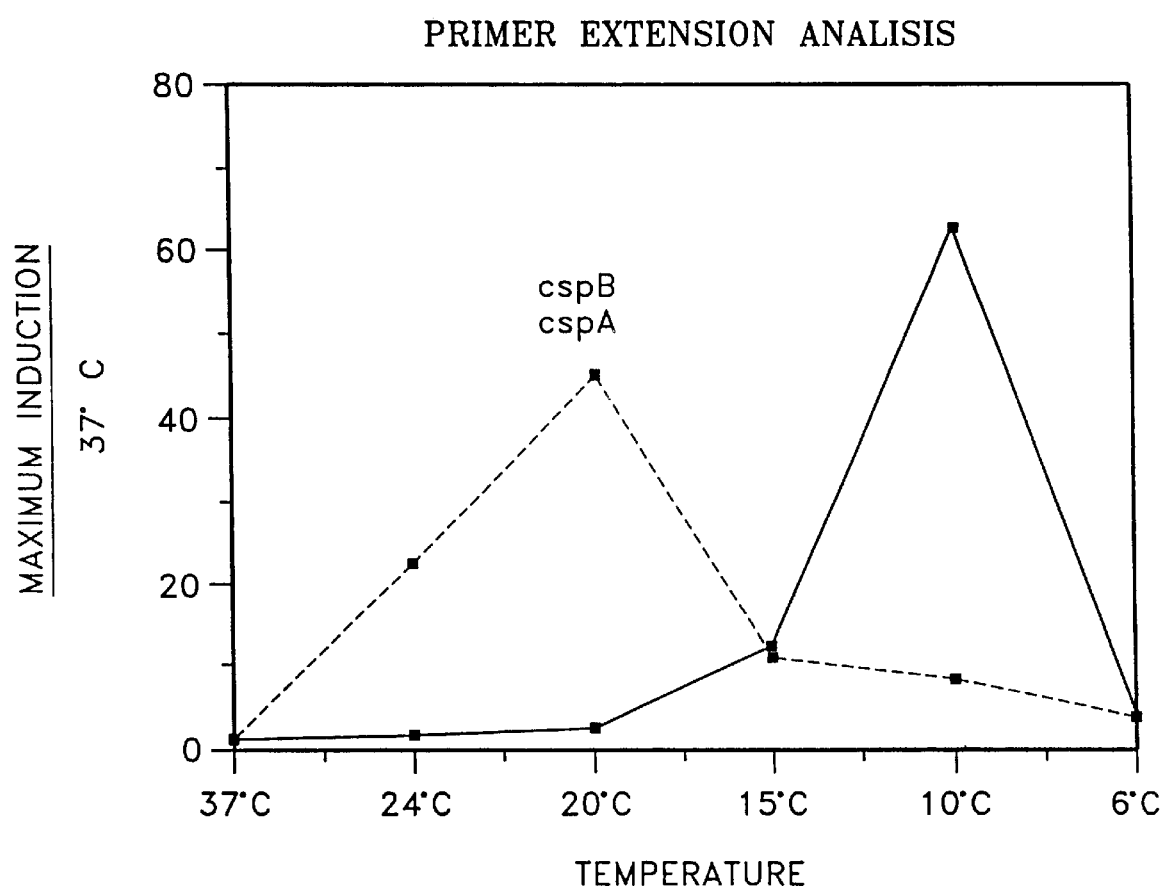
FIG. 2 shows exponentially growing cultures of *E. coli* at different temperatures.

To investigate why two highly homologous proteins, CspA and CspB, appear to have redundant reactions to cold-shock treatment, primer extension analysis was extended to include shifts from 37° C. to various lower temperatures. Cell cultures were grown at 37° C., shifted to 24° C., 20° C., 15° C., 10° C., or 6° C. and samples collected. Total RNA was harvested for each point during the time course for each independent temperature shift (i.e. 24° C., 20° C., 15° C., 10° C., or 6° C.) and the fold induction was expressed as a ratio between the maximum induction at each cold-shock temperature and that observed at 37° C. Interestingly, it was observed that induction of CspA peaked at 20° C. whereas CspB expression peaked at 10° C. (FIG. 2). Thus, the expression of the CspA and CspB genes is differentially regulated at different temperatures, suggesting that E. coli may have a mechanism for detecting temperature variations and responding by regulating gene expression levels.

Figure 3:
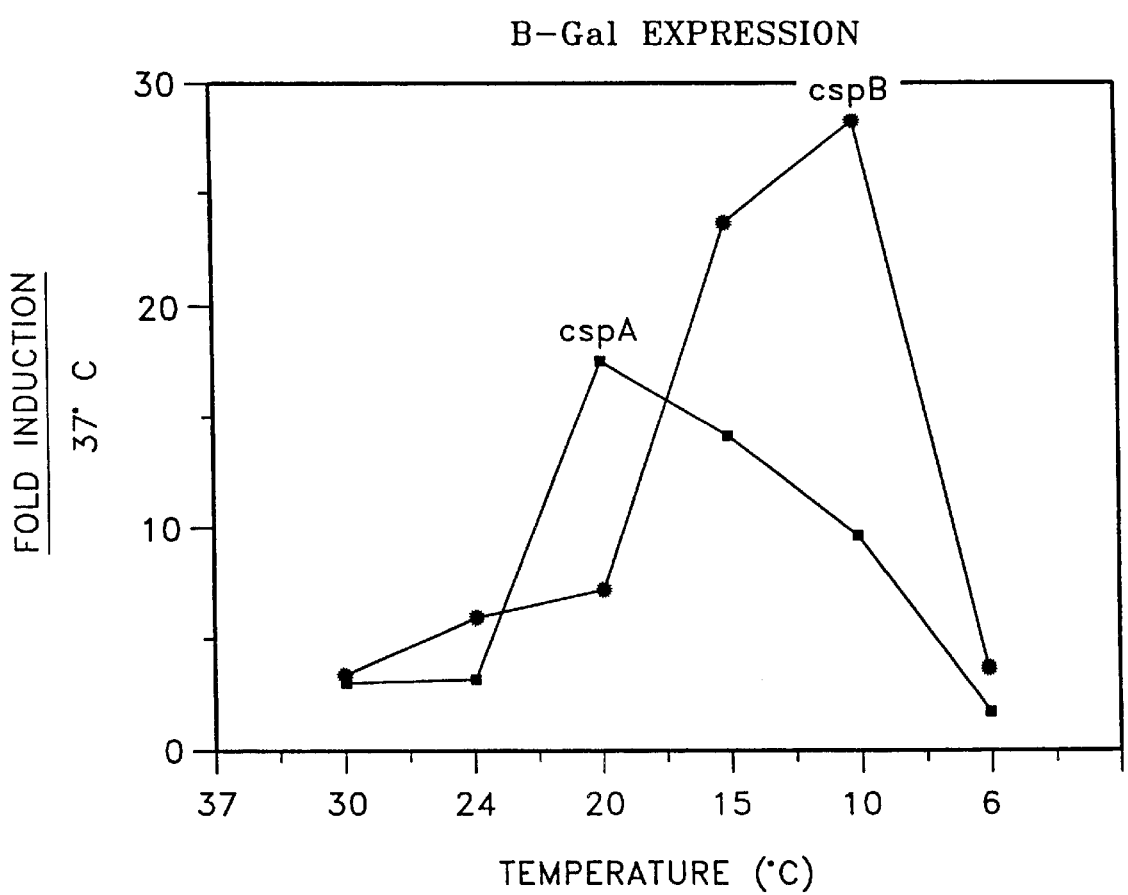
FIG. 3 shows lacZ translation fusions of CspA and CspB.

To investigate this possibility, and to determine whether the pattern of CspA and CspB mRNA induction agrees with the pattern of protein production after cold-shock treatment at different temperatures lacz translation fusions of CspA and CspB were constructed (Li et al., 1994). β-galactosidase expression levels from the CspA and CspB promoters were consistent with the mRNA levels observed by primer extension at different temperatures (FIG. 3). Therefore, a linear correlation between the amount of CspA and CspB mRNA and their corresponding protein productions exist during cold-shock induction.

This result strongly suggests that although CspA and CspB are highly homologous genes and are both regulated at the level of transcription they have different gene expression patterns. This implies the existence of a thermoregulation system in E. coli which can adapt to low temperatures.

Figure 4:
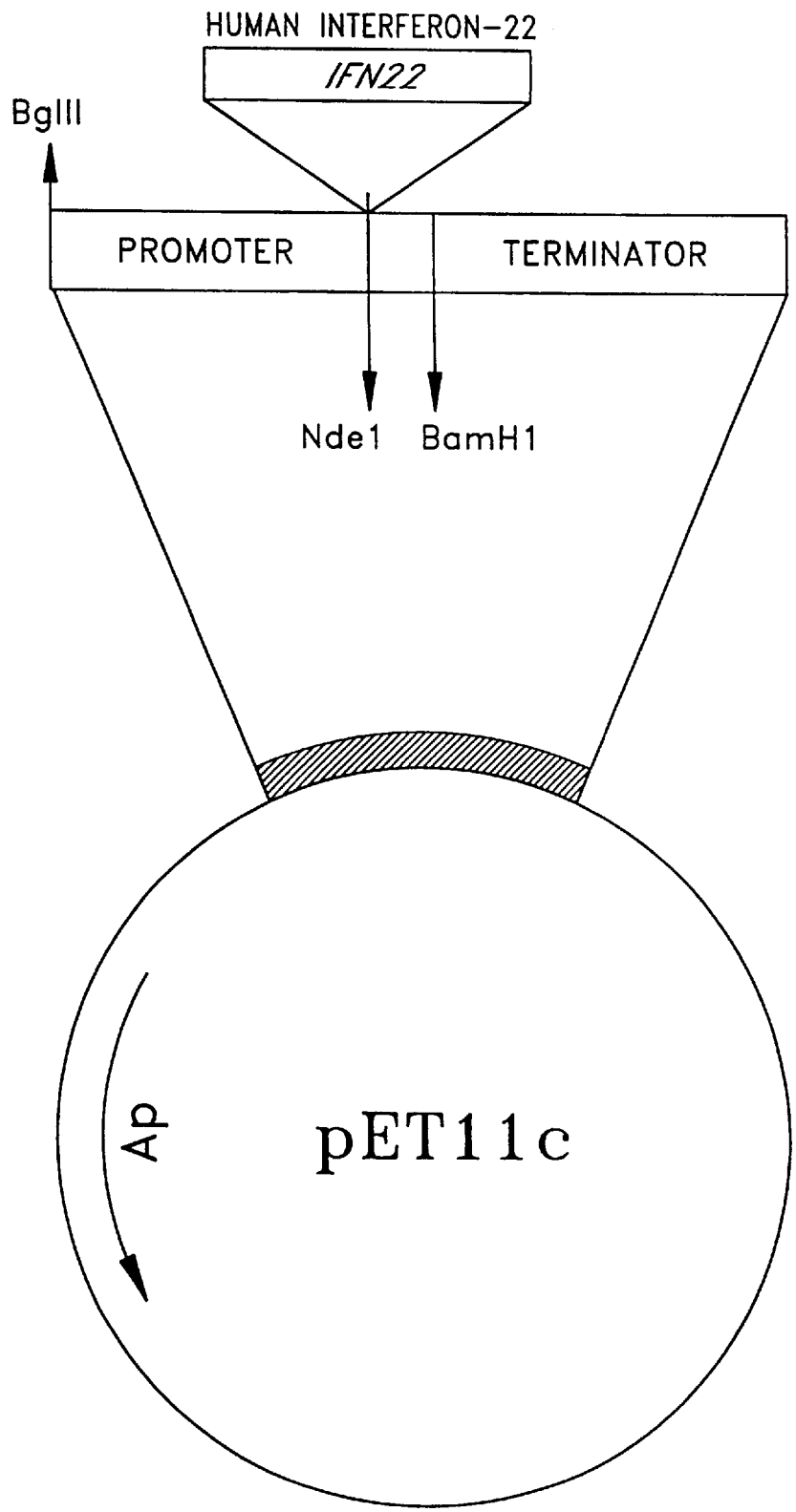
FIG. 4 shows a cold-shock vector which carries the promoter of CspA and CspB, respectively.

The promoters of CspA and CspB are effective to drive the expression of genes other than β-galactosidase. A "cold-shock" vector pET11c was constructed in which the T7 promoter was replaced by the CspA promoter and CspB, respectively driving the expression of the gene for human interferon α-2, which has been shown to be soluble at higher temperature. FIG. 4 shows the construction of the vector.

It is evident that the promoters of the Csp proteins like CspA and CspB are useful to control the expression of target genes to express proteins at temperatures below the normal physiological growth temperatures for the organism selected to express the target protein, whether a prokaryote or an eukaryote, like yeast. This is of particular interest in cases where the target protein has a tendency to become physiologically or biologically inactive (partly or totally) for any of several reasons. For instance, the protein may be susceptible to enzymatic denaturation (e.g. proteolytic) at physiological temperature or the target protein may be improperly folded to a physiologically inactive (or less active) configuration at physiological growth temperature.

The promoters which are induced otherwise than by cold-shock, like Csp C and CspD are useful to direct the synthesis of large amounts of mRNA corresponding to the target gene. The promoters described herein form therefore a family of promoters useful in numerous applications in which promoters are useful. See, *Current Protocols,* in Molecular Biology, Ausbel et al., Unit 16.

DETAILED FIGURE LEGENDS

FIGS. 1, 2, 3, 5 and 6 are described herein in the text.

FIG. 4—Construction of Cold-shock Vector

To construct the cold-shock vector, the following fragments were first amplified by polymerase chain reaction (PCR) for each CsP gene; from nucleotide 1 to 616 for CspA gene, and from nucleotide 1 to 527 for CspB gene. Primers were designed such that a BgIII site was added at nucleotide 1 for CspA and for CspB; and a NdeI site at nucleotide 616 for CspA and at nucleotide (527) for CspB. Therefore, to construct the CspA cold-shock vector, the BqIII-NdeI fragment of vector pET11c (ref. for pETR11C-Studier, F. W. Rosenbert, A. H. Dunn, J. J. and Dubendoff, J. W. (1990) Methods Enzymol. 185, 60–89) was removed and replaced with the BgIII-NdeI fragment of CspA. To construct the CspB)cold-shock vector, the BgIII-NdeI site of vector pETIIc. Therefore, to place expression of any gene under cold-shock regulation, the DNA fragment corresponding to the coding region is cloned at the NdeI or the bamHI site or the NdeI-BamHI site of the cold-shock vector.

Figure 8:
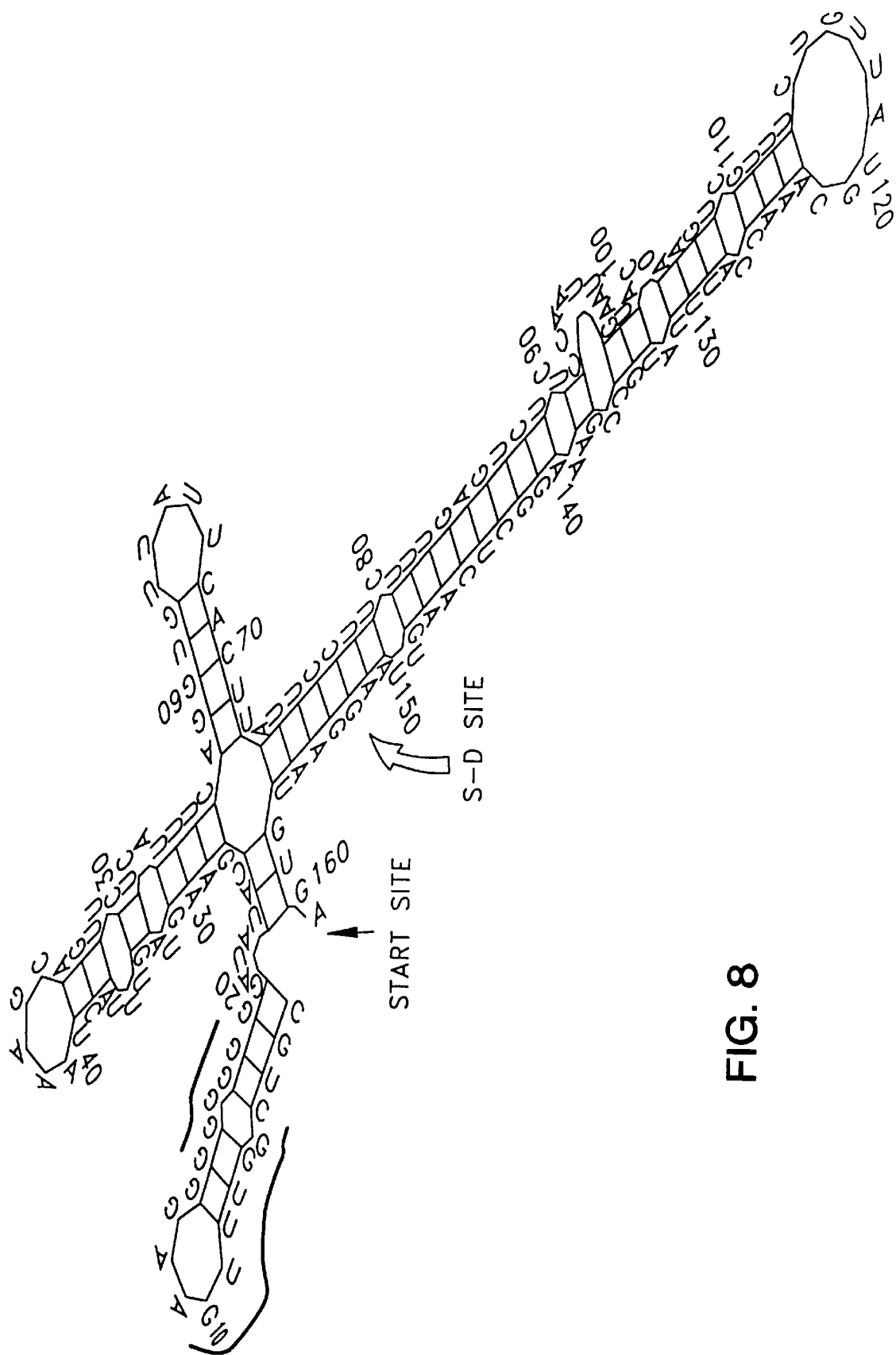
FIG. 8 shows the CspB leader region.
Figure 9A:
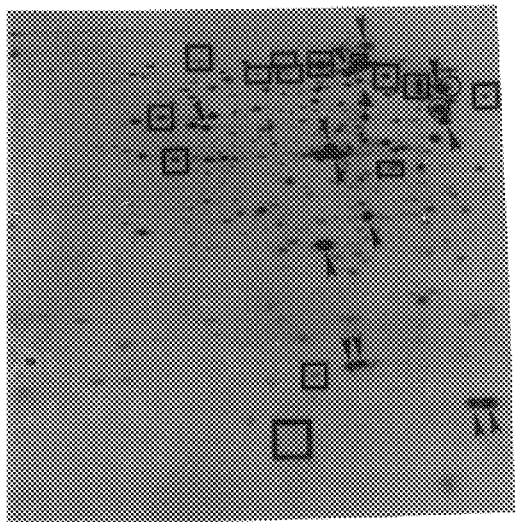
FIG. 9 shows 4 autoradiograms made from two-dimensional gels of total gel extracts of individual protein cultures following a downward shift of temperature.
Figure 9B:
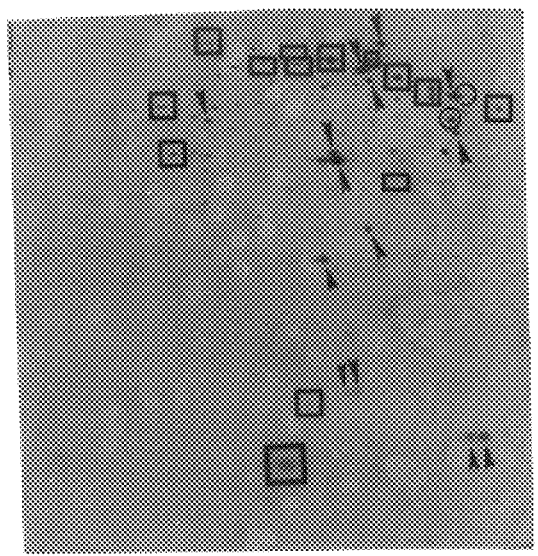
Figure 9C:
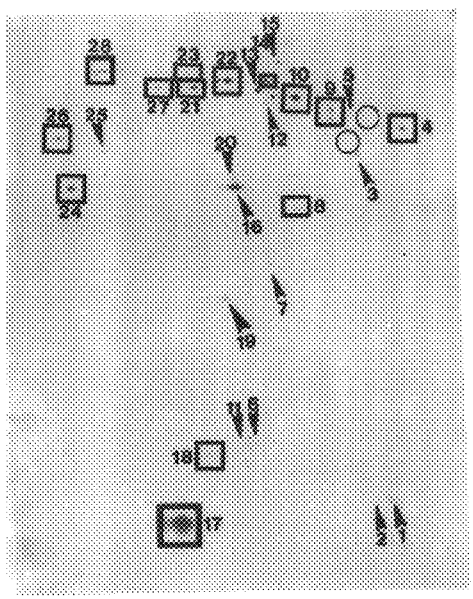
Figure 9D:
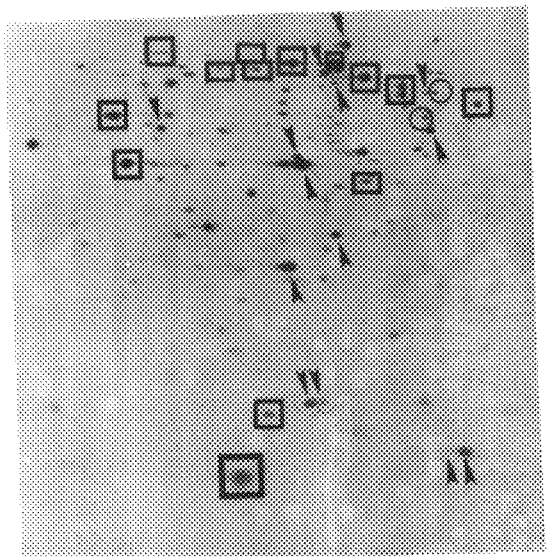

FIGS. 7 and 8—CspA Leader Region: Corresponds to the 5' untranslated region beginning at nucleotide position 457 (see CspA sequence) and ending at nucleotide position 616.

CspB Leader Region: corresponds to the 5' untranslated region beginning at nucleotide position 366 (see CspB sequence) and ending at nucleotide position 527.

The leader regions of CspA and CspB have the potential to form various stem loops which are very similar especially the first loop which has the following nucleotide sequences in common: CGGUUUGA and ACAGAC.

FIG. 9—shows the synthesis of individual proteins following a shift from 37 to 10° C. The autoradiograms were made from two-dimensional gels of total cell extracts of cultures labeled with [35S]methionine before or at various times after the shift. (A) Labeled 5 min preshift. (B) Labeled 0 to 30 min postshift. (C) Labeled 120 to 150 min post shift. (D) Labeled 240 to 270 min postshift. Cellular extracts were prepared and applied to IEF tubes gels containing 1.6% pH 5–7 and 0.4% pH 3.5–10 ampholines and focused to equilibrium. The tube gels were then applied to sodium dodecyl sulphate/polyacrylamide (11.5%) second dimension gels. The numbered spots are the following polypeptides (Jones et al., 1987; La Teana et al., 1991; Jones et al., 1992b): 1, ribosomal protein L7; 2, ribosomal protein L12; 3, trigger factor; 4, NusA; 5, ribosomal protein S1; 6, ribosomal protein S6B; 7, EF-Ts; 8, RecA; 9, dihydrolipoamide acetyltransferase; 10, polynucleotide phosphorylase; 11, ribosomal protein S6A; 12, D74.0; 13, EF-G; 14, GyrA; 15, b-subunit of RNA polymerase; 16, EF-Tu; 17, CspA(F10.6); 18, H-NS; 19, F24.5; 20, F43.8; 21; F84.0; 22, pyruvate dehydrogenase-lipoamide; 23, initiation factor 2b; 24, G41.2; 25, G50.5; 26, G55.0; 27, G74.0; 28, initiation factor 2a. Proteins whose differential rate of synthesis increased, cold-shock proteins, are enclosed in boxes. Other proteins that were continually synthesized, which include many transcriptional and translational proteins, are designated by arrows. Heat shock proteins DnaK and GroEL, whose synthesis was repressed, are enclosed in circles.

FIG. 10 shows a comparison of E. coli CspA with other CspA-like proteins. The deduced amino acid sequence of CspA gene product of E. coli was compared with CspB, CspC, and CspD from E. coli (Lee et al., 1993); with CspB from B. subtilis (Willimsky et al., 1992); with SC7.0 from S.

*calvuligerus* (Avgay et al., 1992); and with the "cold-shock domain" of YB1 from *H. sapiens* (Wistow, 1990; Wolffe et al., 1992).

FIG. 11 shows the nucleotide sequence and the deduced amino acid sequence of CspB.

FIG. 12 shows the nucleotide sequence and the deduced amino acid sequence of CspC.

Figure 13:
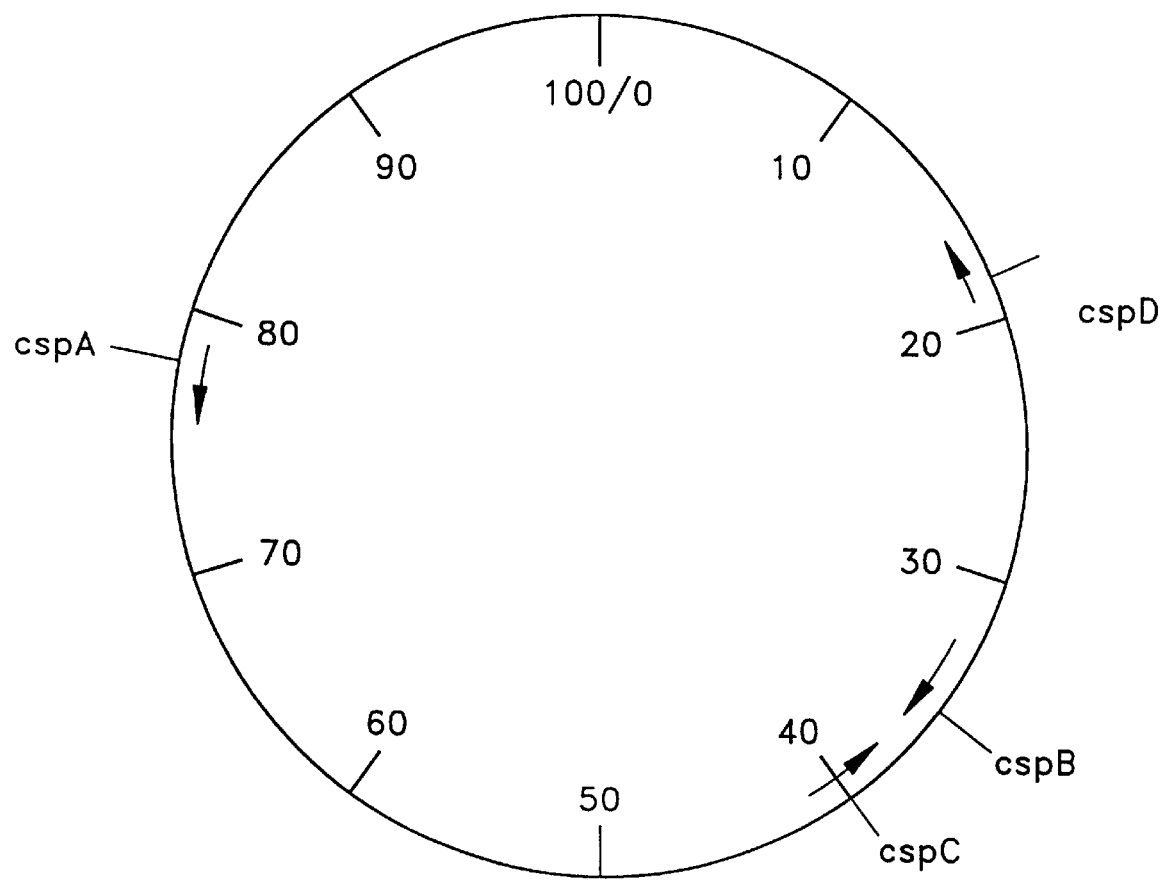
FIG. 13 shows chromosomal locations and the direction of transcription of Csp genes of *E. coli* based upon the location of Kohara's λ phages.

FIG. 13 shows the chromosomal locations and the direction of transcription of Csp genes of *E. coli* based upon the location of Kohara's λ phages.

Figure 14:
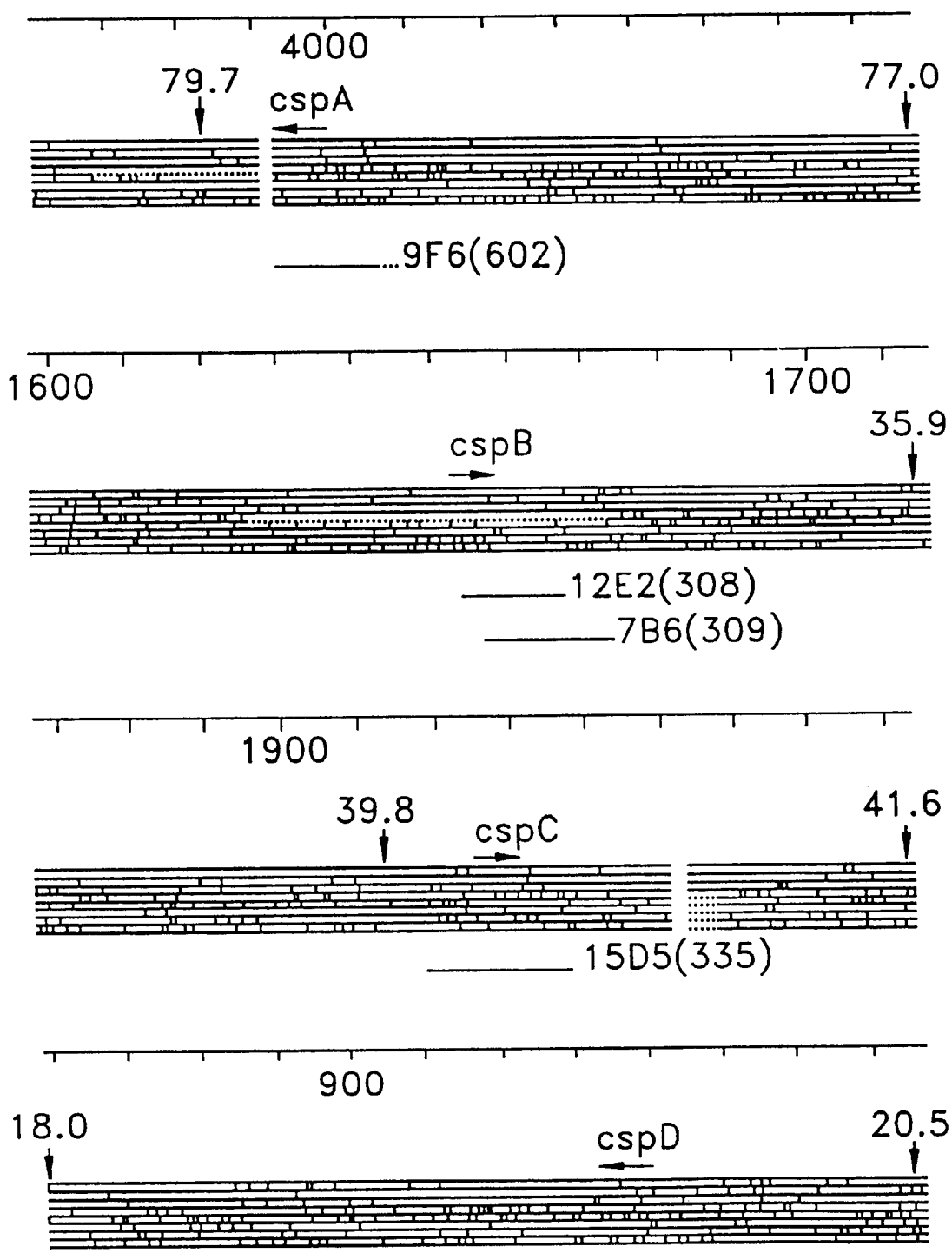
FIG. 14 shows the positions of Csp genes of *E. coli* on the Kohara restriction map (Kohara et al., 1987). The CspA gene was located on Kohara phage 9F6(602) (Goldstein et al., 1990). The CspB gene was located on Kohara phage 12E2 (308) and 7BC(309). The CspC gene was located on Kohara phage 15D5(335).

FIG. 14 shows the positions of Csp genes of *E. coli* on the Kohara restriction map (Kohara et al., 1987). The CspA gene was located on Kohara phage 9F6(602) (Goldstein et al., 1990). The CspB gene was located on Kohara phage 12E2 (308) and 7BC(309). The CspC gene was located on Kohara phage 15D5(335).

FIG. 15 shows the β-galactosidase induction of Csp-lacZ translation fusions after temperature shift from 37° C. to 15° C. At a mid-exponential phase, cultures of *E. coli* SG480 harboring various plasmids grown at 37° C. in L broth were transferred to a incubator-shaker at 15° C. One-ml samples were taken at times indicated for the β-galactosidase assay (Miller, 1992).

EXPERIMENTAL PROCUDURE AND TECHNIQUES

For the Experimental Protocols, see the co-filed manuscripts and publications which are incorporated herein by reference. DNA sequencing, protein purification were all performed by standard protocols. Also see, Tanabe et al. (1992) and references cited therein.

A number of embodiments have been illustrated herein. It is contemplated that one skilled in the art can readily make variations thereof without departing from the spirit and the scope of the invention.

REFERENCES

\* Copy is filed herewith

1. Ang, D. et al. (1991) J. Biol Chem 266: 24233–24236.
2. Avgay, Y., Aharonowitz, Y., and Cohen, G. (1992) Streptomyces contain a 7.0 kDa cold-shock protein. Nucl. Acid Res. 20:5478.
3. Broeze, R. J. et al. (1978) J. Bacteriol. 134: 861–874.
4. Cashel, M. and Rudd, K. E. (1987) The Stringent Response. In *Escherichia coli* and *Salmonella typhimurium:* cellular and molecular biology. Neidhardt, F. C., Ingraham, J. L., Low, K. B., Magasanik, B., Schaechter, M. and Umbarger, H. E., (eds). Washington, D.C.: American Society for Microbiology, pp. 1410–1438.
5. Clouter, J. et al. (1992) Rhizobia. Appli. Envir. Microbiol. 58: 2846–2853.
6. Danyluk, J. et al. (1991) Biochem. Cell. Biol. 69: 383–391.
7. Deschamps, S., Viel, A., and leMaire, M. (1991) Purification-two thermostable components of messenger ribonucleoprotein particles (mRNPs) from Xenopus laevis oocytes, belonging to a novel class of RNA binding proteins. FEBS Lett. 282:110–114.
8. Didier, D. K., Schiffenbauer, J. Woulfe, S. L., Zacheis, M. J. and Schwartz, D. B. (1988) Characterization of the cDNA encoding a protein binding to the major histocompatibility complex class II Y-box. Proc. Natl. Acad. Sci. USA 85:7322–7326.
9. Donovan, W. P., & Kushner, S. R. (1986) Proc. Natl. Acad. Sci. USA 86: 120–124.
10. Doniger, J., Landsman, D., Gonda, M. A., and Wistow, G. (1992) The product of unr, the highly conserved gene upstream of N-ras, contains multiple repeats similar to the cold-shock domain (CSD), a putative DNA-binding motif. The New Biologist 4: 389–395.
11. Dreyfuss, G. et al. (1993) Annu. Rev. Biochem. 62: 289–321.
12. Friedman, D. I. et al. (1984) Microbiol Rev. 48:299–325.
13. Friedman, H. et al. (1969) Nature 233: 909–913.
14. Friedman, H. et al. (1971) J. Mol. Biol. 61: 105–121.
15. Georgopoulos, C. (1992) Trends Biochem. Sci. 17: 295–299.
16. Gething, M. J. et al. (1992) Nature 355: 33–45.
*17. Goldstein, J., Pollitt, N. S., and Inouye, M. (1990) Major cold-shock protein of *Escherichia coli*. Proc. Natl. Acad. Sci. USA 87: 283–287.
18. Gottesman, S., Clark, W. P., and Maurizi, M. R. (1990) The ATP-dependent Clp protease of *Escherichia coli*. J. Biol. Chem. 265: 7886–7893.
19. Gross, C. A. et al. (1990) The function and regulation of heat shock proteins in *Escherichia coli*. In Stress Proteins in biology and medicine. Morimoto, R., Tissieres, A., Georgopoulos, C (eds). Cold Spring Harbor, N.Y.: Cold Spring Harbor Laboratory, pp. 166–190.
20. Grunberg-Manago, M. (1987) Regulation of the expression of aminoacyl-tRNA synthetases and translation factors. In *Escherichia coli* and *Salmonella typhimurium:* celluluar and molecular biology. Neidhardt, F. C., Ingraham, J. L., Low, K. B., Magasanik, B., Schaechter, M. and Umbarger, H. E., (eds). Washington, D.C.: American Society for Microbiology, pp. 1386–1409.
21. Gualerzi, C. O., and Pon, C. L. (1990) Biochemistry 29:5881–5889.
22. Herendeen, S. L. et al. (1979) J. Bacteriol. 139: 185–194.
*23. Jiang, W. et al. (1993) J. Bacteriol. 177:6824–5828
*24. Jones, P. G., VanBogelen, R. A., and Neidhardt, F. C. (1987) Induction of proteins in response to low temperature in *Escherichia coli*. J. Bacteriol. 169: 2092–2095.
*25. Jones, P. G., et al. (1992a) J. Bacteriol. 174: 3903–3914.
*26. Jones, P. G. et al. (1992b) J. Bacteriol. 174: 5798–5802.
27. Julseth, C. R., and Inniss, W. E. (1990) Can. J. Microbiol. 36: 519–524.
28. Kohara, Y., Akiyama, K., and Isono, K. (1987) The physical map of the whole *E. coli* chromosome: Application of a new strategy for rapid analysis and sorting of a large genomic library. Cell 50: 495–508.
29. Kondo, K., and Inouye, M. (1991) J. Biol. Chem. 266: 1737–1744.
30. Kondo, K., and Inouye, M. (1992) J. Biol, Chem. 267: 16252–16258.
31. Kondo, K. et al. (1992) J. Biol Chem. 267: 16259–16265.
32. Kowalski, L. R. Z. et al. (1993) manuscript submitted.
33. Landsman, D. (1992) Nucleic Acids Res. 20: 2861–2864.
34. La Teana, A., et al. (1991) Proc. Natl. Acad. Sci. USA 88: 10907–10911.
35. Lee, S. J. et al. (1993) manuscript submitted.
36. Lemaux, P. G. et al. (1978) Cell 13: 427–434.
37. Lopilato, J., Bortuer, S., and Beckwith, J. (1986) Mutations in a new chromosomal gene of *Escherichia coli* K-12, pcnB, reduced plasmid copy number of pBR322 and its derivatives. Mol. Gen Genet. 205: 285–290.
38. Lund, E., and Kjeldgaard, N. O. (1972) Eur. J. Biochem. 26: 316–326.
39. Mackow, E. R., and Chang, F. N. (1983) Mol. Gen. Genet. 192: 5–9.
40. Maniak, M., and Nellen, W. (1988) Mol. Cell. Biol. 8: 153–159.

41. Maniatis, T., Fritsch, E. F., and Sambrook, J. (1982) Molecular Cloning: A Laboratory Manual. Cold Spring Harbor Laboratory, Cold Spring Harbor, N.Y. Miller, J. H. (1972) Experiments in Molecular Genetics pp. 352–355, Cold Spring Harbor Laboratories, Cold Spring Harbor, N.Y.
42. Murray, M. T., Schiller, D. L. and Franke, W. W. (1992) Sequence analysis of cytoplasmic mRNA-binding proteins of Xenopus oocytes identifies a family of RNA, binding proteins. Proc. Natl. Acad. Sci. USA 89: 11–15.
43. Namura, Y., and Mizusawa, S. (1985) EMBO J. 4: 527–532.
44. Neidhart, F. C., and VanBogelen, R. A. (1987) Heat Shock Response. In *Escherichia coli* and *Salmonella typhimurium:* celluluar and molecular biology. Neidhardt, F. C., Ingraham, J. L., Low, K. B., Magasanik, B., Schaechter, M. and Umbarger, H. E., (eds). Washington, D.C.: American Society for Microbiology, pp. 1334–1345.
45. Newkirk, K., et al. (1993) manuscript submitted.
46. Ng, H., et al. (1962) J. Bacteriol. 84: 331–339.
47. Niki, H., et al. (1991) EMBO J. 10: 183–193.
48. Pao, C. C., and Dyess, B. T. (1981) J. Biol. Chem. 256: 2252–2257.
49. Patterson, T. A., and Dean M. (1987) Preparation of high titer phage lysates. Nucl. Acids Res. 15: 6298.
50. Qoronfleh, M. W. et al. (1992) J. Bacteriol. 174: 7902–7909.
51. Ranjan, M., et al. (1993) Genes & Development 7: 1–12.
52. Roberts, M. E. and Inniss, W. E. (1992) Curr. Microbiol. 25: 275–278.
53, Salerno, G. L., and Pontis, H. G. (1988) Plant Physiol. 89: 648–651.
54. Sanger, F., Nicklen, S., and Coulsen, A. R. (1977) DNA sequencing with chain-terminating inhibitors. Proc. Natl. Acad. Sci. USA 74: 5463–5467.
*55. Schindelin, H., Marahiel, M. A., and Heinemann, U. (1993) Universal nucleic acid-binding domain revealed by crystal structure of the *B. subtilus* major cold-shock protein. Nature 364: 164–168.
56. Schindelin, H, Cordes, F, Jiang, W., Inouye, M., and Heinemann, U. (1993b) manuscript submitted.
*57. Schnuchel, A., Wiltscheck, R., Szisch, M., Herrler, M., Willimsky, G., Graumann, P., Marahiel, M. A., and Holak, T. A. (1993) Structure in solution of the major cold-shock protein from *Bacillus subtilus.* Nature 364: 169–171.
58. Schmid, M. B. (1990) Cell 63: 451–453.
59. Schnier, J. (1987) J. Gen. Microbiol. 133: 3151–3158.
60. Simons, R. W., Houman, F., and Kleckner, N. (1987) Improved single and multicopy lac-based cloning vectors for protein and operon fusions. Gene 53: 85–96.
61. Shaw, M. K., & Ingraham, J. L. (1965) J. Bacteriol. 90: 141–146.
62. Shaw, M. K., and Ingraham, J. L. (1967) J. Bacteriol. 94:157–164.
63. Squires C., and Squires, C. (1992) J. Bacteriol. 174: 1081–1085.
64. Stanier R. Y. et al. (1976) The microbial world, 4th. ed., Prentice-Hall, Inc., Englewood Cliffs, N.J.
65. Sugino, A. et al. (1977) Proc Natl Acad Sci USA 74: 4767–4771.
66. Tafuri, S. R., and Wolffe, A. P. (1990) Xenopus Y-box transcription factors: Molecular cloning, functional analysis, and developmental regulation, Proc. Natl. Acad. Sci. USA 87: 9028–9032.
67. Takata, R. T. et al. (1985) Nucleic Acids Res. 13: 7289–7296.
*68. Tanabe, H., Goldstein, J., Yang, M., and Inouye, M. (1992) Identification of the promoter region of the *Escherichia coli* major cold-shock gene, cspA. J. Bacteriol. 174: 3867–3873.
69. VanBogelen, R. A. and Neidhardt, F. C. (1990) Proc. Natl. Acad. Sci. USA 87: 5589–5593.
70. Vieira, J., and Messing, J. (1982) The pUC plasmids, and m14mp7-derived system for insertion mutagenesis and sequencing with synthetic universal primers. Gene 19: 259–268.
71. Walker, G. C. (1984) Microbial. Rev. 48: 60–93.
72. Westphal, M. et al. (1986) FEBS Lett 209: 92–96.
73. Willimsky, G., Bang, H., Fischer, G., and Marahiel, M. A. (1992) Characterization of cspB, a *Bacillus subtilis* inducible cold-shock gene affecting cell viability at low temperatures. J. Bacteriol. 174: 6326–6335.
74. Wistow, G. (1990) Nature 344: 823–824.
75. Wolffe, A. P., Tafuri, S., Ranjan, M., and Familari, M. (1992) The Y-box factors: A family of nucleic acid binding proteins conserved from *Escherichia coli* to man. New Biol. 4: 290–298.

We claim:

1. An isolated DNA molecule comprising a prokaryotic promoter wherein said promoter is induced under conditions that elicit a cold shock response, wherein said conditions comprise a decrease in temperature below the normal physiological growth temperature of the bacterium.

2. An isolated DNA molecule comprising a prokaryotic promoter of claim 1 wherein said promoter is induced under conditions that elicit a cold shock response and comprises nucleotides 1–566 of cspB (SEQ ID NO: 1).

3. An isolated DNA molecule comprising a prokaryotic promoter induced under conditions that elicit the cold shock response, wherein the promoter comprises nucleotides 1–534 of CspA (SEQ ID NO: 19).

4. An isolated promoter of claim 3 wherein the cold-shock is a decrease in temperature of at least 13° C.

5. An isolated promoter of claim 3 wherein the cold-shock is a decrease in temperature to about 15° C. or below.

6. A plasmid comprising the promoter of claim 3.

7. An isolated DNA molecule comprising a prokaryotic promoter, wherein said promoter is induced under conditions that elicit a cold shock response, said promoter comprising the nucleic acid sequences TTGCTT-17 base pairs-GTTAAT.

8. A vector comprising an isolated DNA molecule comprising a prokaryotic promoter, wherein said promoter is induced under conditions that elicit a cold shock response, said promoter comprising the nucleic acid sequence TTGCTT-17 base pairs-GTTAAT.

9. An isolated DNA cold-shock promoter which comprises the TTGCTT-17 base pairs-GTTAAT sequences.

10. A plasmid comprising the promoter of claim 9.

11. An isolated DNA molecule comprising a promoter derived from a prokaryotic cell, wherein said promoter is repressed under conditions that elicit a cold shock response, wherein said conditions comprise a decrease in temperature below the normal physiological growth temperature of said prokaryotic cell.

\* \* \* \* \*

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 877 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 528..740

-continued (xi) SEQUENCE DESCRIPTION: SEQ ID NO: 1:

```
AGCTTTAATA TAGCTCATGA AAGGTAAACA TTGGCAGCTG AAGGGCCACG CAGACCATTT      60

ATCCGGCAAA ATTCCACGCG TAATCCGGTG GTAATTTCTT CTGCATCGCG GAGATTGAGC     120

GCTGAAACAT GAAGCTGGAC ATCGATACGA CCATCGGATG GGGTGATAAG ACCCTTGCCG     180

CTTTTGCCGT CAAAGGTTTT GACAATTCCT GTCATTTTAC GGGACAAAAA AATTCCTTAA     240

TACTGATAAC TTGGCGCACT ATACACACGT TCCTGAAGAA AGCTATAGTT TTTTGATGGG     300

GTTGAAGATG GCTGGATGTC TAAAATAAAC ATTGCTTCAT ATGTTCAACT ATGCGTTAAT     360

GATTGCGTCG GTTTGAAGAA CAGACGATAT ACGAAGTAGT TTACTAAAGC AGTTCTCATT     420

TCAGGTGTTA TTCACTTATT CCTTCTTTGA GTCTCTCCAA TTAAGTACGA AGTCGTTTCT     480

GTTATGCAAA CCATTTATGC CGAAAGGCTC AAGTTAAGGA ATGTAGA ATG TCA AAT       536
                                                  Met Ser Asn
                                                   1
```

```
AAA ATG ACT GGT TTA GTA AAA TGG TTT AAC GCT GAT AAA GGT TTC GGC      584
Lys Met Thr Gly Leu Val Lys Trp Phe Asn Ala Asp Lys Gly Phe Gly
     5                  10                  15

TTT ATT TCT CCT GTT GAT GGT AGT AAA GAT GTG TTT GTG CAT TTT TCT      632
Phe Ile Ser Pro Val Asp Gly Ser Lys Asp Val Phe Val His Phe Ser
 20              25                  30                  35

GCG ATT CAG AAT GAT AAT TAT CGA ACC TTA TTT GAA GGT CAA AAG GTT      680
Ala Ile Gln Asn Asp Asn Tyr Arg Thr Leu Phe Glu Gly Gln Lys Val
             40                  45                  50

ACC TTC TCT ATA GAG AGT GGT GCT AAA GGT CCT GCA GCA GCA AAT GTC      728
Thr Phe Ser Ile Glu Ser Gly Ala Lys Gly Pro Ala Ala Ala Asn Val
         55                  60                  65

ATC ATT ACT GAT TAAAATTCAT CGCTCGTCTG TATACGATAA CGAAGAAGGC           780
Ile Ile Thr Asp
         70

TGATGCCTGA GTAGAGATAC GGACAGAGTA GTGAATATTG GATCTCTTTA ATAAAAAGTA     840

AGGAGGTCCA ATACATGAAA CAATGGCTAG CATATTT                              877
```

(2) INFORMATION FOR SEQ ID NO: 2:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Asn Lys Met Thr Gly Leu Val Lys Trp Phe Asn Ala Asp Lys
 1               5                  10                  15

Gly Phe Gly Phe Ile Ser Pro Val Asp Gly Ser Lys Asp Val Phe Val
                 20                  25                  30

His Phe Ser Ala Ile Gln Asn Asp Asn Tyr Arg Thr Leu Phe Glu Gly
             35                  40                  45

Gln Lys Val Thr Phe Ser Ile Glu Ser Gly Ala Lys Gly Pro Ala Ala
         50                  55                  60

Ala Asn Val Ile Ile Thr Asp
 65                  70
```

(2) INFORMATION FOR SEQ ID NO: 3:

(i) SEQUENCE CHARACTERISTICS:
        (A) LENGTH: 1120 base pairs
        (B) TYPE: nucleic acid (C) STRANDEDNESS: single
          (D) TOPOLOGY: linear (ii) MOLECULE TYPE: DNA (genomic)

(ix) FEATURE:
          (A) NAME/KEY: CDS
          (B) LOCATION: 686..892

(xi) SEQUENCE DESCRIPTION: SEQ ID NO: 3:

```
CGGGATATCA GCAAAAGATA TTTACCCCAT TAATTTATTA GGATGTTTAC ATCGGATTTG      60

TGATTAAGCG TGGTATTATT TATTACGCGA AACGTTTCTC TCTTGAGGTT TTTGCTCATT     120

CATCAATTTT TCTTATTTTA AATTTACAAT CCTTTGGGGA TTGACTTCTC TTTAGGGTAA     180

TTAATAGCCG TTAACTGACT GTTTTATGAG AAAAAGTGAT ATAACTTTTT ATTCATTGCA     240

TAGCAAAAAA TGTGATATTG CACGCACTAT GTAATAACTT CTCCCACTGG CCTGGAACAA     300

CTGAACTTAT TGAACTATGT TAGAAAATAC GCCAGTTTAA GTATCTGCCT GAACTGGCAA     360

GGTTAAGCAC AATGATATAT CGGCGCGTAT TCCGTTGCAT AAGTGTGCAA AAAAAGTGGA     420

AGACGTATCG AGATTTGTGC GTCTGATCGA GACATGTTTA AAAATGGCTT GCCATAATTA     480

ACGTTGTATG TGATAACAGA TTTCGGGTTA AACGAGGTAC AGTTCTGTTT ATGTGTGGCA     540

TTTTCAGTAA AGAAGTCCTG AGTAAACACG TTGACGTTGA ATACCGCTTC TCTGCCGAGC     600

CTTATATTGG TGCCTCATGC AGTAATGTGT CAGTTTTATC TATGTTATGC CTGCGGCGAA     660

GAAACAATC TAAGGAATTT TTCAA ATG GCA AAG ATT AAA GGT CAG GTT AAG       712
                              Met Ala Lys Ile Lys Gly Gln Val Lys
                                1               5

TGG TTC AAC GAG TCT AAA GGT TTT GGC TTC ATT ACT CCG GCT GAT GGC       760
Trp Phe Asn Glu Ser Lys Gly Phe Gly Phe Ile Thr Pro Ala Asp Gly
 10              15                  20                  25

AGC AAA GAT GTG TTC GTA CAC TTC TCC GCT ATC CAG GGT AAT GGC TTC       808
Ser Lys Asp Val Phe Val His Phe Ser Ala Ile Gln Gly Asn Gly Phe
             30                  35                  40

AAA ACT CTG GCT GAA GGT CAG AAC GTT GAG TTC GAA ATT CAG GAC GGC       856
Lys Thr Leu Ala Glu Gly Gln Asn Val Glu Phe Glu Ile Gln Asp Gly
         45                  50                  55

CAG AAA GGT CCG GCA GCT GTT AAC GTA ACA GCT ATC TGATCGAATC            902
Gln Lys Gly Pro Ala Ala Val Asn Val Thr Ala Ile
     60                  65

CACTGATCTG AAGTGTGAAT ACGCTTCAAT CTCGCTATAA AGCCTCGTCG AATGCGAGGC     962

TTTTTACTAT GCTTTATCTT CGCTCCTGGC GTTCGGATAT TTGCCCGCCG CGTGATTCGC    1022

GTTACACTTG CGGCCTTTAG TATCTGCCGG AGTTGTCATG TCTTTTTCCT GTCCACTTTG    1082

CCATCAGCCT CTTTCGCGTG AAAAAAACAG CTATATCT                            1120
```

(2) INFORMATION FOR SEQ ID NO: 4:

(i) SEQUENCE CHARACTERISTICS:
          (A) LENGTH: 69 amino acids
          (B) TYPE: amino acid
          (D) TOPOLOGY: linear (ii) MOLECULE TYPE: protein (xi) SEQUENCE DESCRIPTION: SEQ ID NO: 4:

```
Met Ala Lys Ile Lys Gly Gln Val Lys Trp Phe Asn Glu Ser Lys Gly
  1               5                  10                  15

Phe Gly Phe Ile Thr Pro Ala Asp Gly Ser Lys Asp Val Phe Val His
                 20                  25                  30
```

-continued

```
Phe Ser Ala Ile Gln Gly Asn Gly Phe Lys Thr Leu Ala Glu Gly Gln
         35                  40                  45

Asn Val Glu Phe Glu Ile Gln Asp Gly Gln Lys Gly Pro Ala Ala Val
     50                  55                  60

Asn Val Thr Ala Ile
 65
```

(2) INFORMATION FOR SEQ ID NO: 5:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO: 5:

```
AACGGUUUGA CGUACAGACC AUUAAAGCAG UGUAGUAAGG CAAGUCCCUU CAAGAGUUAU      60

CGUUGAUACC CCUCGUAGUG CACAUUCCUU UAACGCUUCA AAAUCUGUAA AGCACGCCAU     120

AUCGCCGAAA GGCACACUUA AUUAUUAAAG GUAAUACACU                           160
```

(2) INFORMATION FOR SEQ ID NO: 6:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO: 6:

```
CGUCGGUUUG AAGAACAGAC GAUAUACGAA GUAGUUUACA AAAGCAGUUC UCAUUCAGG       60

UGUUAUUCAC UUAUUCCUUC UUUGAGUCUC UCCAAUUAAG UACGAAGUCG UUUCUGUUAU     120

GCAAACCAUU UAUGCCGAAA GGCUCAAGUU AAGGAAUGUA GA                       162
```

(2) INFORMATION FOR SEQ ID NO: 7:

(i) SEQUENCE CHARACTERISTICS:
        (A) LENGTH: 70 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 7:

```
Met Ser Gly Lys Met Thr Gly Ile Val Lys Trp Phe Asn Ala Asp Lys
 1               5                  10                  15

Gly Phe Gly Phe Ile Thr Pro Asp Asp Gly Ser Lys Asp Val Phe Val
                 20                  25                  30

His Phe Ser Ala Ile Gln Asn Asp Gly Tyr Lys Ser Leu Asp Glu Gly
             35                  40                  45

Gln Lys Val Ser Phe Thr Ile Glu Ser Gly Ala Lys Gly Pro Ala Ala
         50                  55                  60

Gly Asn Val Thr Ser Leu
 65                  70
```

(2) INFORMATION FOR SEQ ID NO: 8:

(i) SEQUENCE CHARACTERISTICS:
        (A) LENGTH: 71 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 8:

```
Met Ser Asn Lys Met Thr Gly Leu Val Lys Trp Phe Asn Ala Asp Lys
1               5                  10                  15

Gly Phe Gly Phe Ile Ser Pro Val Asp Gly Ser Lys Asp Val Phe Val
            20                  25                  30

His Phe Ser Ala Ile Gln Asn Asp Asn Tyr Arg Thr Leu Phe Glu Gly
        35                  40                  45

Gln Lys Val Thr Phe Ser Ile Glu Ser Gly Ala Lys Gly Pro Ala Ala
    50                  55                  60

Ala Asn Val Ile Ile Thr Asp
65                  70
```

(2) INFORMATION FOR SEQ ID NO: 9:

(i) SEQUENCE CHARACTERISTICS:
        (A) LENGTH: 69 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 9:

```
Met Ala Lys Ile Lys Gly Gln Val Lys Trp Phe Asn Glu Ser Lys Gly
1               5                  10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Ile Gln Asp Gly Gln Lys Gly Pro Ala Ala Val
    50                  55                  60

Asn Val Thr Ala Ile
65
```

(2) INFORMATION FOR SEQ ID NO: 10:

(i) SEQUENCE CHARACTERISTICS:
        (A) LENGTH: 74 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 10:

```
Met Glu Lys Gly Thr Val Lys Trp Phe Asn Asn Ala Lys Gly Phe Gly
1               5                  10                  15

Phe Ile Cys Pro Glu Gly Gly Gly Glu Asp Ile Phe Ala His Tyr Ser
            20                  25                  30

Thr Ile Gln Met Asp Gly Tyr Arg Thr Leu Lys Ala Gly Gln Ser Val
        35                  40                  45
```

```
Gln Phe Asp Val His Gln Gly Pro Lys Gly Asn His Ala Ser Val Ile
    50                  55                  60

Val Pro Val Glu Val Glu Ala Ala Val Ala
65              70
```

(2) INFORMATION FOR SEQ ID NO: 11:

(i) SEQUENCE CHARACTERISTICS:
        (A) LENGTH: 66 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 11:

```
Met Ala Thr Gly Thr Val Lys Trp Phe Asn Ala Glu Lys Gly Phe Gly
1               5                   10                  15

Phe Ile Ala Gln Asp Gly Gly Pro Asp Val Phe Val His Tyr Ser
            20                  25                  30

Ala Ile Asn Ala Thr Gly Phe Arg Ser Leu Glu Glu Asn Gln Val Val
            35                  40                  45

Asn Phe Asp Val Thr His Gly Glu Gly Pro Gln Ala Glu Asn Val Ser
        50                  55                  60

Pro Ala
65
```

(2) INFORMATION FOR SEQ ID NO: 12:

(i) SEQUENCE CHARACTERISTICS:
        (A) LENGTH: 67 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 12:

```
Met Leu Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65
```

(2) INFORMATION FOR SEQ ID NO: 13:

(i) SEQUENCE CHARACTERISTICS:
        (A) LENGTH: 74 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 13:

```
Ile Ala Thr Lys Val Leu Gly Thr Val Lys Trp Phe Asn Val Arg Asn
1               5                   10                  15
```

```
Gly Tyr Gly Phe Ile Asn Arg Asn Asp Thr Lys Glu Asp Val Phe Val
                20                  25                  30

His Gln Thr Ala Ile Lys Lys Asn Asn Pro Arg Lys Tyr Leu Arg Ser
            35                  40                  45

Val Gly Asp Gly Glu Thr Val Glu Phe Asp Val Val Glu Gly Glu Lys
    50                  55                  60

Gly Glu Glu Ala Ala Asn Val Thr Gly Pro
65                  70
```

(2) INFORMATION FOR SEQ ID NO: 14:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 14:

```
Asp Gly Ser Lys
1
```

(2) INFORMATION FOR SEQ ID NO: 15:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 15:

```
Tyr Arg Thr Leu
1
```

(2) INFORMATION FOR SEQ ID NO: 16:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 16:

```
Thr Pro Asp Asp
1
```

(2) INFORMATION FOR SEQ ID NO: 17:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 17:

```
Met Ser Gly Lys Met Thr
1               5
```

(2) INFORMATION FOR SEQ ID NO: 18:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 18:

```
Val Lys Trp Phe Asn
1               5
```

(2) INFORMATION FOR SEQ ID NO: 19:

(i) SEQUENCE CHARACTERISTICS:
        (A) LENGTH: 1205 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 617..826

(xi) SEQUENCE DESCRIPTION: SEQ ID NO: 19:

```
AAGCTTCGAT GCAATTCACG ATCCCGCAGT GTGATTTGAG GAGTTTTCAA TGGAATATAA      60

AGATCCAATG CATGAGCTGT TGAGCAGCCT GGAACAGATT GTTTTTAAAG ATGAAACGCA     120

GAAAATTACC CTGACGCACA GAACAACGTC CTGTACCGAA ATTGAGCAGT ACGAAAAGG      180

GACAGGATTA AAAATCGATG ATTTCGCCCG GGTTTTGGGC GTATCAGTCG CCATGGTAAA     240

GGAATGGGAA TCCAGACGCG TGAAGCCTTC AAGTGCCGAA CTAAAATTGA TGCGTTTGAT     300

TCAAGCCAAC CCGGCATTAA GTAAGCAGTT GATGGAATAG ACTTTATCCA CTTATGCTGT     360

TTACGGTCCT GATGACAGAC CGTTTTCCAA CCGATTAATC ATAAATATGA AAAATAATTG     420

TTGCATCACC CGCCAATGCG TGGCTTAATG CACATCAACG GTTTGACGTA CAGACCATTA     480

AAGCAGTGTA GTAAGGCAAG TCCCTTCAAG AGTTATCGTT GATACCCCTC GTAGTGCACA     540

TTCCTTTAAC GCTTCAAAAT CTGTAAAGCA CGCCATATCG CCGAAAGGCA CACTTAATTA     600

TTAAAGGTAA TACACT ATG TCC GGT AAA ATG ACT GGT ATC GTA AAA TGG         649
               Met Ser Gly Lys Met Thr Gly Ile Val Lys Trp
                 1               5                  10

TTC AAC GCT GAC AAA GGC TTC GGC TTC ATC ACT CCT GAC GAT GGC TCT       697
Phe Asn Ala Asp Lys Gly Phe Gly Phe Ile Thr Pro Asp Asp Gly Ser
               15                  20                  25

AAA GAT GTG TTC GTA CAC TTC TCT GCT ATC CAG AAC GAT GGT TAC AAA       745
Lys Asp Val Phe Val His Phe Ser Ala Ile Gln Asn Asp Gly Tyr Lys
           30                  35                  40

TCT CTG GAC GAA GGT CAG AAA GTG TCC TTC ACC ATC GAA AGC GGC GCT       793
Ser Leu Asp Glu Gly Gln Lys Val Ser Phe Thr Ile Glu Ser Gly Ala
       45                  50                  55

AAA GGC CCG GCA GCT GGT AAC GTA ACC AGC CTG TAATCTCTGC TTAAAAGCAC    846
Lys Gly Pro Ala Ala Gly Asn Val Thr Ser Leu
   60                  65                  70

AGAATCTAAG ATCCCTGCCA TTTGGCGGGG ATTTTTTTAT TTGTTTTCAG GAAATAAATA     906

ATCGATCGCG TAATAAAATC TATTATTATT TTTGTGAAGA ATAAATTTGG GTGCAATGAG     966

AATGCGCAAC GCCGTAAGTA AGGCGGGAAT AATTTCCCGC CGAAGACTCT TACTCTTTCA    1026

ATTTGCAGGC TAAAAACGCC GCCAGCTCAT AACTCTCCTG TTTAATATGC AATTCACACA    1086
```

-continued

```
GTGAATCTCT TATCATCCAG GTGAAAAATA AAAGCGTGAA ACAAATCACT ATTAAAGAAA      1146

GTAATCTATA TTTCTGCGCA TTCCAGCTCT GTGTTGATTT CACGAGTATG TACTGCACC       1205
```

(2) INFORMATION FOR SEQ ID NO: 20:

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO: 20:

```
Met Ser Gly Lys Met Thr Gly Ile Val Lys Trp Phe Asn Ala Asp Lys
 1               5                  10                  15

Gly Phe Gly Phe Ile Thr Pro Asp Asp Gly Ser Lys Asp Val Phe Val
            20                  25                  30

His Phe Ser Ala Ile Gln Asn Asp Gly Tyr Lys Ser Leu Asp Glu Gly
        35                  40                  45

Gln Lys Val Ser Phe Thr Ile Glu Ser Gly Ala Lys Gly Pro Ala Ala
    50                  55                  60

Gly Asn Val Thr Ser Leu
65                  70
```